(12) United States Patent
Sahoo et al.

(10) Patent No.: US 9,271,934 B2
(45) Date of Patent: Mar. 1, 2016

(54) WATER DISPERSIBLE GLYCERYL MONOOLEATE MAGNETIC NANOPARTICLE FORMULATION

(71) Applicant: Institute of Life Sciences, Bhubaneswar, Orissa (IN)

(72) Inventors: Sanjeeb Kumar Sahoo, Orissa (IN); Fahima Dilnawaz, Orissa (IN); Abhalami Singh Singh, Orissa (IN)

(73) Assignee: Institute of Life Sciences, Bhubaneswar, Orissa (IN)

( * ) Notice: Subject to any disclaimer, the term of this patent is extended or adjusted under 35 U.S.C. 154(b) by 447 days.

(21) Appl. No.: 13/833,916

(22) Filed: Mar. 15, 2013

(65) Prior Publication Data

US 2013/0302508 A1    Nov. 14, 2013

Related U.S. Application Data

(62) Division of application No. 13/262,660, filed as application No. PCT/IN2009/000639 on Nov. 12, 2009.

(30) Foreign Application Priority Data

May 21, 2009 (IN) .................................. 779/KOL/09

(51) Int. Cl.
| | |
|---|---|
| *A61K 9/14* | (2006.01) |
| *A61K 9/51* | (2006.01) |
| *A61K 9/00* | (2006.01) |
| *A61K 31/231* | (2006.01) |
| *A61K 33/26* | (2006.01) |
| *A61K 49/18* | (2006.01) |

(Continued)

(52) U.S. Cl.
CPC ............... *A61K 9/14* (2013.01); *A61K 9/0009* (2013.01); *A61K 9/5115* (2013.01); *A61K 9/5123* (2013.01); *A61K 9/5192* (2013.01); *A61K 31/231* (2013.01); *A61K 33/26* (2013.01); *A61K 49/1836* (2013.01); *A61K 49/1839* (2013.01); *A61K 49/1866* (2013.01); *A61K 49/1869* (2013.01); *B82Y 5/00* (2013.01); *A61K 9/5094* (2013.01); *A61K 41/0052* (2013.01); *Y10S 977/773* (2013.01); *Y10S 977/906* (2013.01); *Y10S 977/911* (2013.01)

(58) Field of Classification Search
None
See application file for complete search history.

(56) References Cited

U.S. PATENT DOCUMENTS

2008/0213377 A1*  9/2008  Bhatia et al. .................. 424/489

FOREIGN PATENT DOCUMENTS

WO         20080105773  A2      9/2008

OTHER PUBLICATIONS

W Wu, Q He, C Jiang. "Magnetic Iron Oxide Nanoparticles: Synthesis and Surface Functionalization Strategies." Nanoscale Research Letters, vol. 3, 2008, pp. 397-415, published online Oct. 2, 2008.*

(Continued)

*Primary Examiner* — Isaac Shomer
(74) *Attorney, Agent, or Firm* — The Webb Law Firm

(57) ABSTRACT

The present invention is an aqueous dispersible magnetic nanoparticle formulation with a high drug loading capacity used for sustained drug delivery. The formulated magnetic nanoparticles are composed of an iron oxide core coated with a long chain polymer, which provides aqueous dispersibility without the use of surfactant. A method is developed for the functionalization of magnetic nanoparticles for use in biomedical field.

8 Claims, 18 Drawing Sheets

(f)

Figure 1:
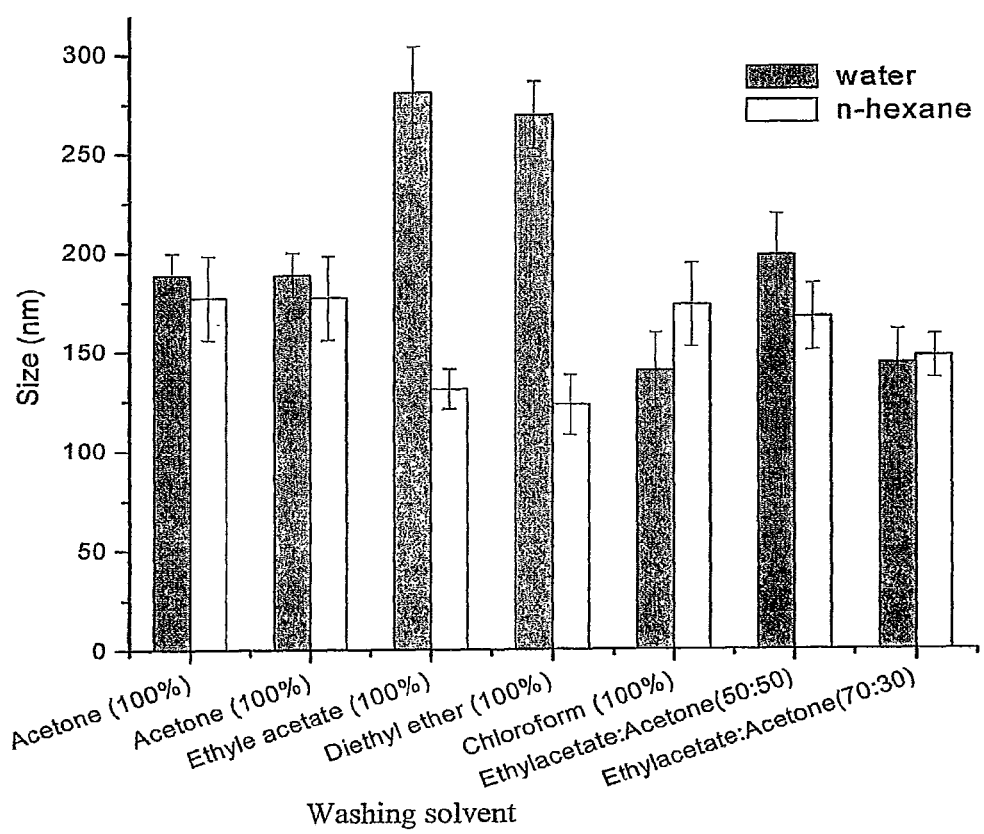

(51) Int. Cl.
 *B82Y 5/00* (2011.01)
 *A61K 41/00* (2006.01)
 *A61K 9/50* (2006.01)

(56) References Cited

OTHER PUBLICATIONS

TK Jain, MA Morales, SK Sahoo, DL Leslie-Pelecky, V Labhasetwar. "Iron Oxide Nanoparticles for Sustained Delivery of Anticancer Agents." Molecular Pharmaceutics, vol. 2 No. 3, 2005, pp. 194-205.*

Jain et al., "Iron Oxide Nanoparticles for Sustained Delivery of Anticancer Agents," Molecular Pharmaceutics, Jan. 18, 2005, pp. 194-205, vol. 2, No. 3.

Dilnawaz et al., "Dual Drug loaded Superparamagnetic Iron Oxide Nanoparticles for Targeted Cancer Therapy," Biomaterials, 2010, pp. 3694-3706, vol. 31.

* cited by examiner (f)

(a)

(b)

(a)

(b)

(a)

(b)

(a)

(b)

WATER DISPERSIBLE GLYCERYL MONOOLEATE MAGNETIC NANOPARTICLE FORMULATION

CROSS REFERENCE TO RELATED APPLICATIONS

This application is a divisional of U.S. patent application Ser. No. 13/262,660, filed Oct. 13, 2011, which is the U.S. national stage application of PCT/IN2009/000639, filed Nov. 12, 2009, which claims priority to Indian Application No. 779/KOL/09, filed May 21, 2009. Each of the above applications is incorporated by reference herein.

FIELD OF INVENTION

This invention relates to a method for preparing a water dispersible glyceryl monooleate (GMO) Magnetic nanoparticles (MNPs) formulation and use of the same.

BACKGROUND OF THE INVENTION

Magnetic nanoparticles (MNPs) are emerging as promising candidates for their applications in biomedical research encompassing of drug delivery, magnetic resonance imaging, cell mechanics, hyperthermia, in vivo tracking of stem cells, tumor progression, nucleic acid (DNA and RNA) separation and cell separations, due to their ultra fine sizes, biocompatibility and superparamagnetic behaviour. Another important property which makes magnetic nanoparticles ideal for biomedical applications is their low toxicity. The MNPs can have high level of accumulation in the target tissues or organ due to their host cell tropism and biophysical nature, which helps for the most promising application of these magnetic nanoparticles in site-specific drug delivery.

For drug delivery, the magnetic nanoparticles are required to have high magnetization values, size smaller than 100 nm and narrow distributions of particle size. To these nanoparticles, a pharmaceutical drug can be loaded on to the surface which could be driven to the target organ and released there. An external localized magnetic field gradient may be applied to a chosen site to attract drug-loaded magnetic nanoparticles from blood circulation, by reducing their systemic distribution and offering a possibility of administering lower but more accurately targeted dose. In this process, the magnetic nanoparticles should bear superparamagnetic property i.e, they do not retain any magnetic property when the magnetic filed is removed.

Drug targeting to tumors and its other related pathological conditions, is desirable since anticancer agents demonstrate nonspecific toxicities that significantly limit their therapeutic potentials. For these applications, the size, charge and surface chemistry of the magnetic nanoparticles are particularly important, which strongly affects both the blood circulation time as well as the bioavailability of the particles within the body. It is envisioned that nanoparticles can be surface-modified so that it could to simultaneously function as contrast enhancement agent and drug carrier, allowing real-time monitoring of tumor response to drug treatment.

Surface coating is an integral part of all MNP formulations meant for biomedical applications. The colloidal electro stabilization arising from repulsion of the surface charge are not sufficient enough to prevent aggregation in the biological solution due to presence of salts and other electrolytes that may neutralize the charge. Furthermore, on intravenous injection the MNP is subjected to the adsorption of plasma protein or opsonization as a first step of clearance by the reticuloendothelial system (RES). Accordingly evading the uptake by RES and maintaining a long plasma half life is a major challenge for many MNP applications in drug delivery. So, a polymeric coating over the MNPs is required for providing steric barrier and to prevent nanoparticle agglomeration, thereby avoiding opsonization. Also these coatings provide a way to functionalize the surface of MNPs such as surface charge and chemical functionalization. Therefore, to improve their biocompatibility and injectibility magnetic nanoparticles are generally coated with hydrophilic polymers such as starch or dextran, polyethyleneglycol (PEG), streptavidin, poly-L-lysine (PLL), poly ethylene imide (PEI), and the therapeutic agents of interest which are chemically conjugated or conically bound to the outer layer of polymer. This approach is complex, involves multiple steps with a very little drug loading capacity, and the bound drug dissociates within hours. Fast release of drug from the carrier system may be less effective, especially in the tumor therapy, where drug retention is required for therapeutic efficacy. Entrapping the magnetic nanoparticles into other sustained release polymeric drug carrier systems such as nanoparticles formulated from poly-dl-lactide-co-glycolide (PLGA), polylactides (PLL), polylactic acid (PLA), or in dendrimers results in significant loss in magnetization of the core magnetic material. Also in silica coated magnetic nanoparticles there is decrease in magnetization which has the limitation for the effective targeting in drug delivery system.

Various monomeric species such as bisphosphonates, dimercaptosuccinic acid and aloxysilane have been evaluated to facilitate the anchoring and attachment of polymers on MNP. But coating of the particle with monomeric species does not allow colloidal stability at physiological pH. Coating the particles with large molecules, such as polymers or surfactants containing long-chain hydrocarbons, helps to prevent aggregation of the particles in biological solution thereby offering more effective stabilization. Therefore, different research groups mostly use long chain polymer such as oleic acid and its salt for the stabilization of iron oxide nanoparticles. Gupta et al have synthesized magnetic nanoparticles by coprecipitation method using sodium oleate for forming stable dispersion of magnetic nanoparticles. Jain et al have developed oleic acid (OA)-pluronic (F-127) stabilized iron oxide magnetic nanoparticle formulation where they have entrapped some of the hydrophobic drugs which partitioned into it without any loss of magnetization. As in their study they found that after a coating of OA, still these formulations were not well dispersible in water, so they have used pluronic types of surfactants to get water based formulation. The pluronic acid anchors at the interface of the OA shell and give the aqueous dispersibility and easy load of hydrophobic anticancer agents. Experimental evidences show that higher doses of pluronic (F-127) have toxic effects towards human erythrocytes and there is an elevation of cholesterol and triglycerides in the blood plasma.

Therefore, with an aim of getting colloidal stability of the magnetic nanoparticles without use of any surfactant, a different polymeric lipid molecule was used for coating of the MNPs. Synthetic lipid glyceryl monooleate (GMO) approved by food and drug administration (FDA), is an emulsifier, flavouring agent for the food industry and excipient agent for antibiotics. The ionic polymer GMO also possesses bioadhesive properties that can be used to enhance the therapeutic efficacy of the dosage forms by increasing the contact time at the targeted tissues. Glyceryl monooleate (GMO) is an unsaturated monoglyceride belonging to the class of water-insoluble amphiphilic lipids. Depending on the water content and temperature it forms different types of lyotropic liquid crystals. As water content and temperature increase, it system forms cubic phase via reversed micellar and lamellar phases. The cubic liquid crystalline phase is highly viscous, thermodynamically stable, and insensitive to salts and solvents and coexists in equilibrium with excess of water and resistant to physical degradation. The high viscosity of GMO provides sustained release of drugs due to slow drug diffusion or increased residence time in its solubilized form. The heterogeneous structure of GMO in water permits incorporation of both hydrophilic and hydrophobic drugs or a combination and their presence does not induce a change in lyotropic phase structure. GMO is a metabolite during lipolysis of triglycerides. Also, GMO itself is an object of lipolysis due to different kinds of esterase activity. Hence, the cubic phase made of GMO is biodegradable and, as such a potential candidate for use in drug delivery systems. GMO has a similar long chain polymer structure as that of oleic acid, mainly used in the formulation of MNPs. Keeping in view of these properties of GMO; we have coated the magnetic nanoparticles with GMO by replacing OA. We have developed a novel aqueous based ultrafine stable magnetic nanoparticle formulation with a coating of GMO without the use of any surfactant. The aqueous solubility of the particle is achieved by the complete removal of the un-adsorbed GMO during the washing process with the use of different organic solvents during the synthesis process. We hypothesize that, GMO coated MNP will be a ideal delivery system for the treatment of cancer as the hydrophobic drug would partition into the GMO coating and would provide aqueous dispersibility of the solutions without any loss of magnetization and at the same time drug loaded MNPs can be used as a novel drug delivery system with the help of external magnetic field.

Bioseparation

MNPs are beneficial in biomedical research for separating out the specific biological entities from their native environment in order to concentrate the samples for further analysis. It is possible due to attraction between an external magnetic field and the MNPs which enables the separation of a wide variety of biological entities. Use of biocompatible MNPs is one of the ways to achieve this. It is a two step process involving i) tagging or labeling of the desired biological entities with magnetic material and ii) separating out these tagged entities via fluid based magnetic separation devices. Labeling is achieved through the surface modification of magnetic nanoparticles with dextran, phospholipids and Polyvinyl alcohol (PVA) which provides the link between the particles and the target site on a cell or molecules. To aim for specific binding on the surface of the cells, the help of antibody and antigen specificity action can be taken into account. For active binding the cells are targeted with biological molecules such as hormones and folic acid. Precision binding of antibodies specifically to their corresponding antigens provides an accurate way to label cells e.g MNPs coated with immunospecific agents have been successfully bound to red blood cells HIV-tat peptides, lung cancer, bacteria, urological cancer cells and golgi vesicles. The magnetic separation of target cells from mixtures, such as peripheral blood, isolation of cancer cells in blood samples or stem cells in bone marrow has considerable practical potential in improved diagnosis in biomedical research. When combined with microfluidic technology, low-field magnetic separations could enable faster and less expensive processing of tissue samples for biomarker detection. Furthermore, MNPs can be biologically activated to allow the uptake of cells via endocytic pathways, thereby allowing certain cellular compartments to be specifically addressed. Once taken up, the desired cellular compartments can be magnetically isolated and accurately studied using proteomic analysis. There are two main challenges to make all the above-discussed biomedical applications come true: a) a good synthesis route for manufacturing monodisperse MNPs with diameters <10 nm; and b) a good method to functionalize the surface of the nanoparticles. The latter determines the ability of the MNPs to interact in a well-defined and controllable manner with living cells and to be used for the cell separation. We have functionalized acid groups on the surface of the GMO coated magnetic nanoparticles by the use of DMSA (2, 3 meso mercapto succinic acid) which can be further conjugated with the primary amine groups of any peptide or protein etc.

OBJECTS OF THE INVENTION

An object of this invention is to propose a method for the preparation of glyceryl monooleate (GMO) magnetic nanoparticles (MNPs) formulation;

Another object of this invention is to propose a method for the preparation of glyceryl monooleate (GMO) magnetic nanoparticles (MNPs) formulation having good aqueous dispersibility;

Still another object of this invention is to propose a method for the preparation of glyceryl monooleate (GMO) magnetic nanoparticles (MNPs) formulation which can effectively be used as a carrier for both the hydrophilic and hydrophobic drugs;

Further, object of this invention is to propose a method for the preparation of glyceryl monooleate (GMO) magnetic nanoparticles (MNPs) formulation which has no toxicity;

Yet another object of this invention is to functionalize the formulation and then to attach any protein or peptide.

SUMMARY OF THE INVENTION

The resulted magnetic nanoparticles formulation further can be loaded with different therapeutic drugs and functionalized with different chemical groups for further conjugate with different peptides, proteins or targeting moiety.

According to this invention there is provided a method for preparing a water dispersible glyceryl monooleate (GMO) magnetic nanoparticles formulation comprising an iron oxide particle core coated with long chain polymer for producing an aqueous dispersible magnetic nanoparticle formulation.

A method for preparing glyceryl monooleate (GMO) magnetic nanoparticles (MNPs) formulation comprising:
heating a mixture of Fe (III) and Fe (II) with constant stirring under $N_2$ atmosphere;
adding ammonium hydroxide to the said mixture;
adding glyceryl monooleate (GMO) to the suspension drop wise;
subjecting the mixture to the step of stirring under $N_2$ atmosphere;
washing the formulation several times with combination of ethylacetate and acetone (70:30) to wash the excess glyceryl monooleate (GMO);
subjecting the washed formulation to the step of lyophilization to yield powder form.

BRIEF DESCRIPTION OF THE ACCOMPANYING DRAWING

FIG. 1: Effect of washing in different organic solvents on size of glyceryl monooleate (GMO) magnetic nanoparticles (MNPs) in water and n-hexane measured by laser light scattering (data as mean±SEM, n=3).

Figure 2:
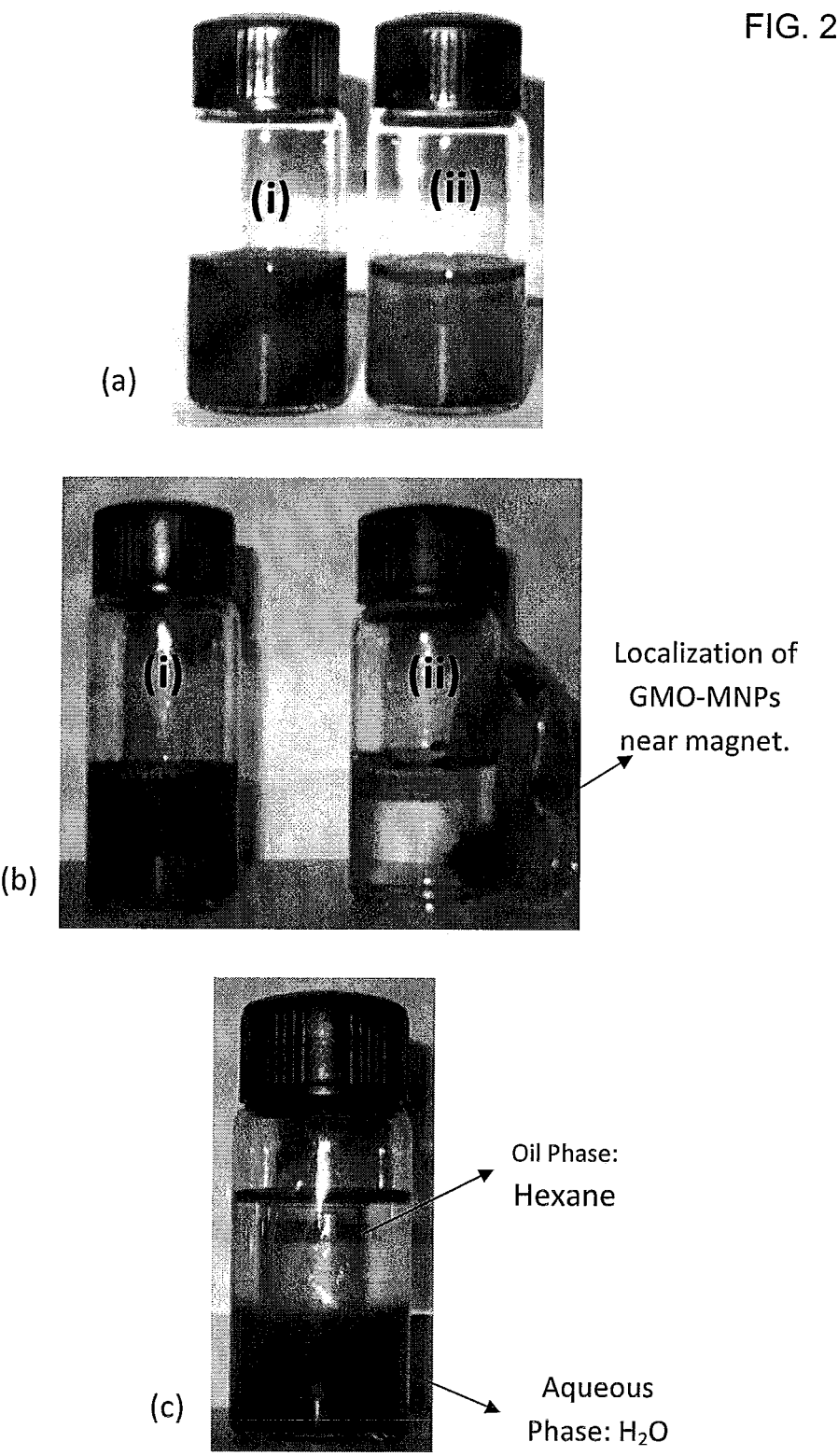

FIG. 2: (a) water solubility test. (i) After sonication
(ii) Settling down of particles after one month
(10 mg of glyceryl monooleate (GMO) magnetic nanoparticles (MNPs) dispersed in 10 ml of Milli Q water, sonicated in ice bath for 30 seconds, kept for one month. Even after one month they demonstrated excellent colloidal stability in an aqueous phase).
(b) Localization of glyceryl monooleate (GMO) magnetic nanoparticles (MNPs) near magnet (NdFeB).
(i) Without magnet
(ii) With magnet
(c) Solubility test of magnetic nanoparticles in oil and water phase. (10 mg of glyceryl monooleate (GMO) magnetic nanoparticle (MNP) dispersed in 10 ml of Milli Q water, sonicated in ice bath for 30 seconds. To this 10 ml of hexane was added. As the hexane has lower density than water it goes up and shows a phase separation. As the formulated particles are water dispersible they remain in the aqueous phase).

Figure 3:
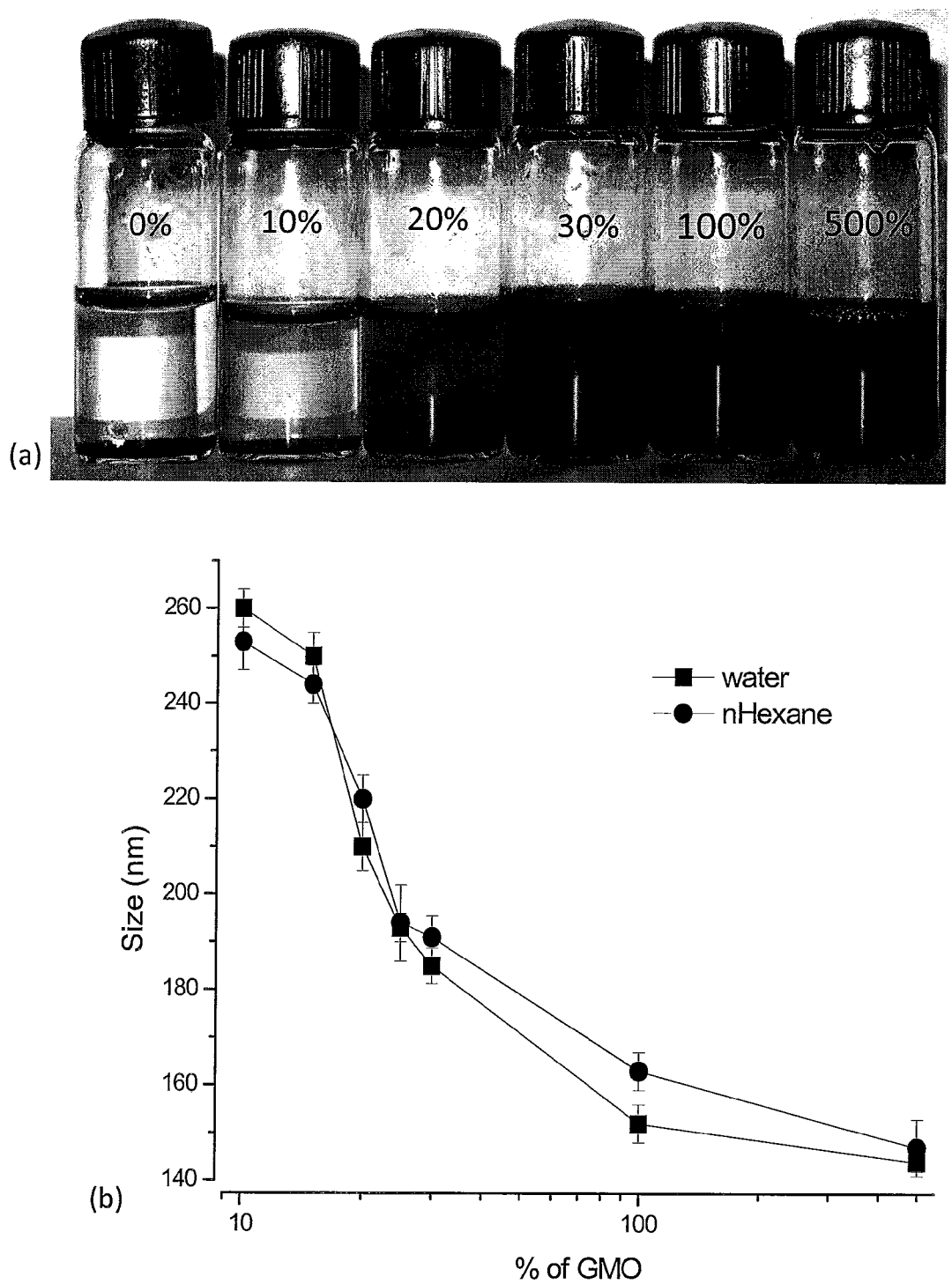

FIG. 3: (a) Effect of GMO conc. On sedimentation of MNPs in water.
(b) Mean particle size of glyceryl monooleate (GMO) magnetic nanoparticles (MNPs) in water and n-hexane measured by laser light scattering (data as mean±SEM, n=3).

Figure 4:
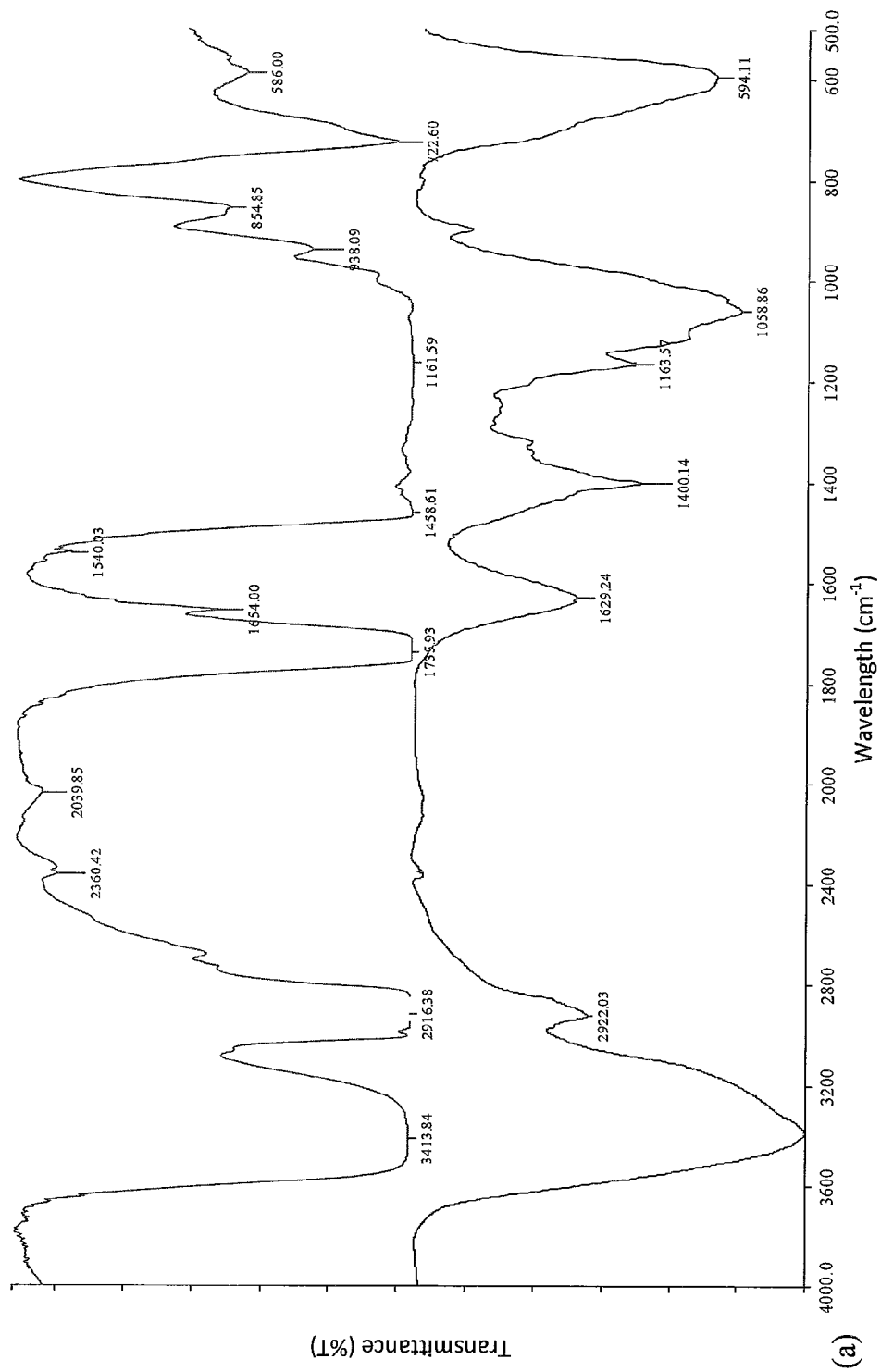
Figure 4:
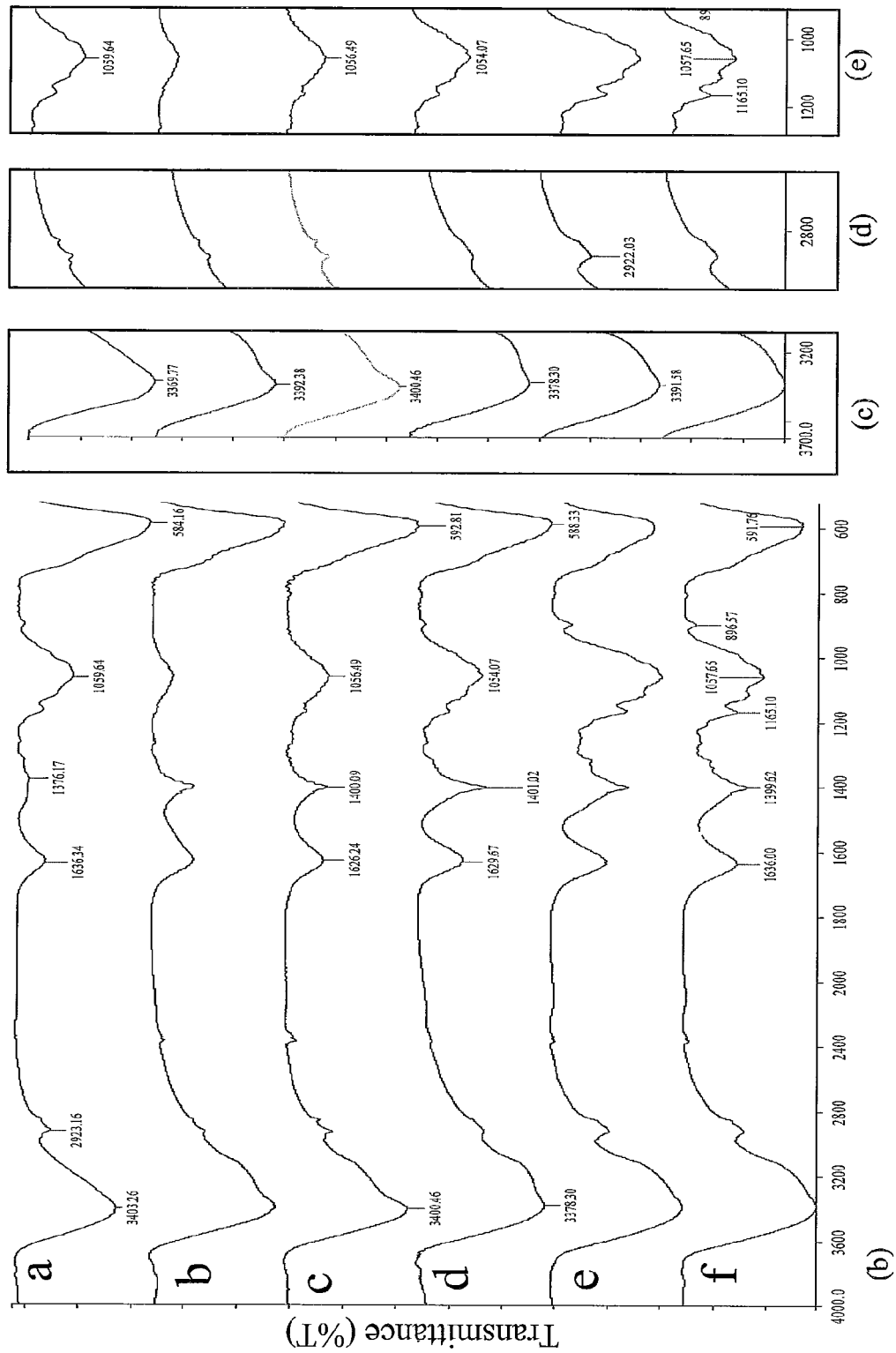
Figure 4:
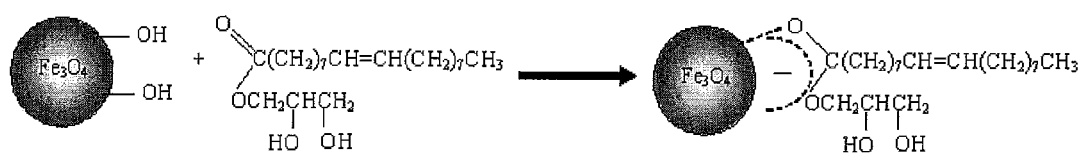

FIG. 4: (a) FT-IR spectra of a) pure GMO and b) GMO-MNPs.
(b) FT-IR spectra of GMO coated MNPs: a) Uncoated MNPs, b) 10% GMO coated MNP, c) 15% GMO coated MNP, d) 20% GMO coated MNP, e) 25% GMO coated MNP and f) 100% GMO coated MNP.
(c) Zoom of the FTIR spectra in the range of 3700 $cm^{-1}$ to 3200 $cm^{-1}$.
(d) Zoom of the FTIR spectra in the range of 2800 $cm^{-1}$.
(e) Zoom of the FTIR spectra in the range of 1200 $cm^{-1}$ to 1000 $cm^{-1}$.
(f) Schematic representation of chemisorption of GMO on to the MNP surface.

Figure 5:
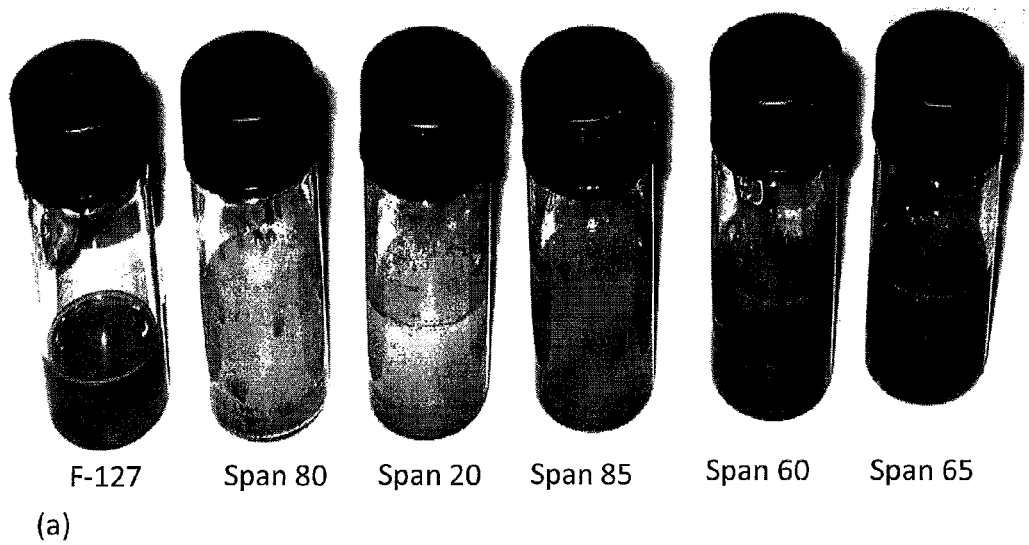
Figure 5:
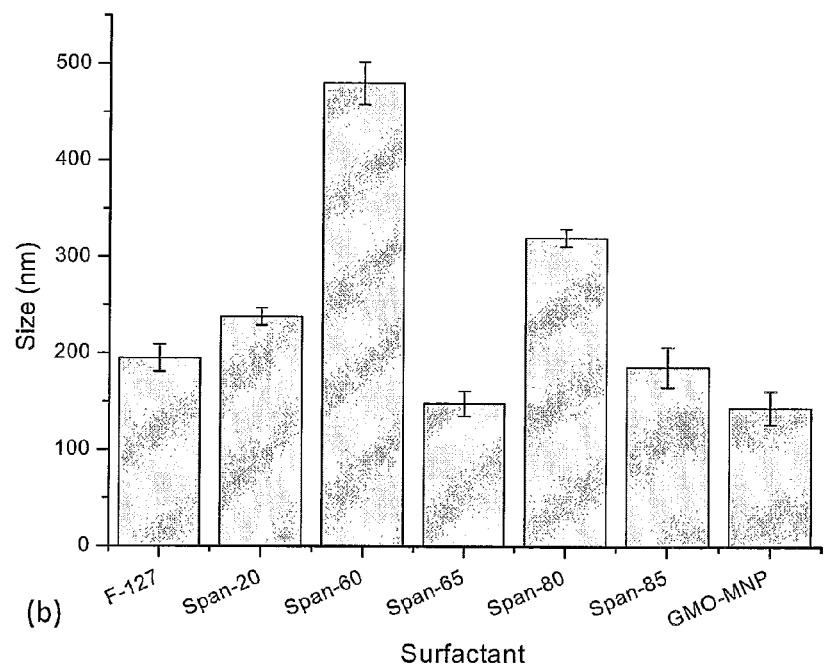

FIG. 5: (a) Effect of different surfactants on the dispersibility of glyceryl monooleate (GMO) magnetic nanoparticles (MNPs) in water.
(b) Effect of different surfactants on the size of glyceryl monooleate (GMO) magnetic nanoparticles (MNPs) in water.

Figure 6:
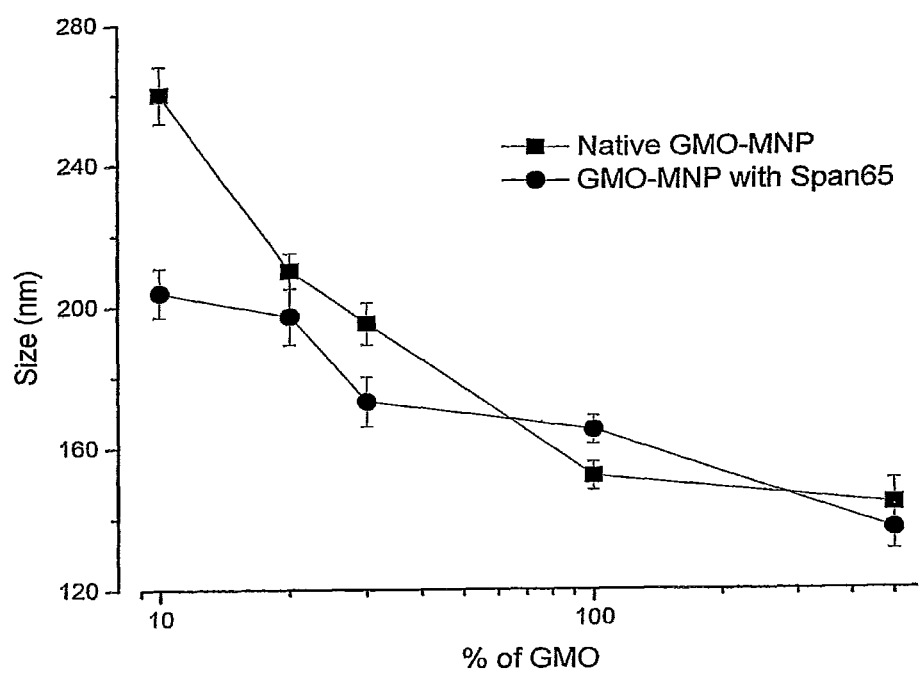

FIG. 6: Comparison of size of different percentage (w/w) GMO coated MNPs with and without surfactant Span 65.

Figure 7:
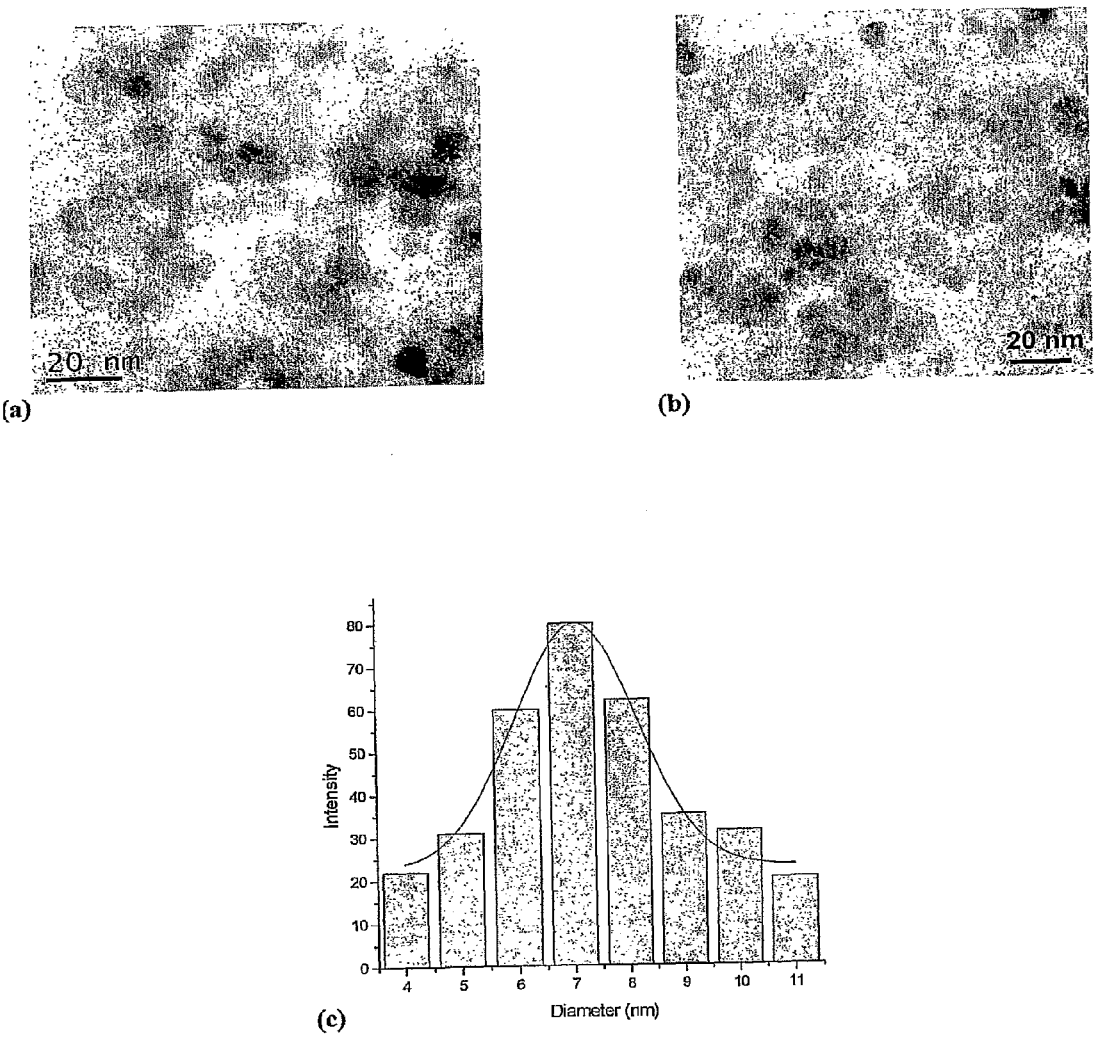

FIG. 7: (a) TEM of Iron oxide particles in water.
(b) TEM of Iron oxide particles in n-hexane.
(c). Particle size distribution of glyceryl monooleate (GMO) magnetic nanoparticles (MNPs) measured by TEM (Average values of twenty measurements).

Figure 8:
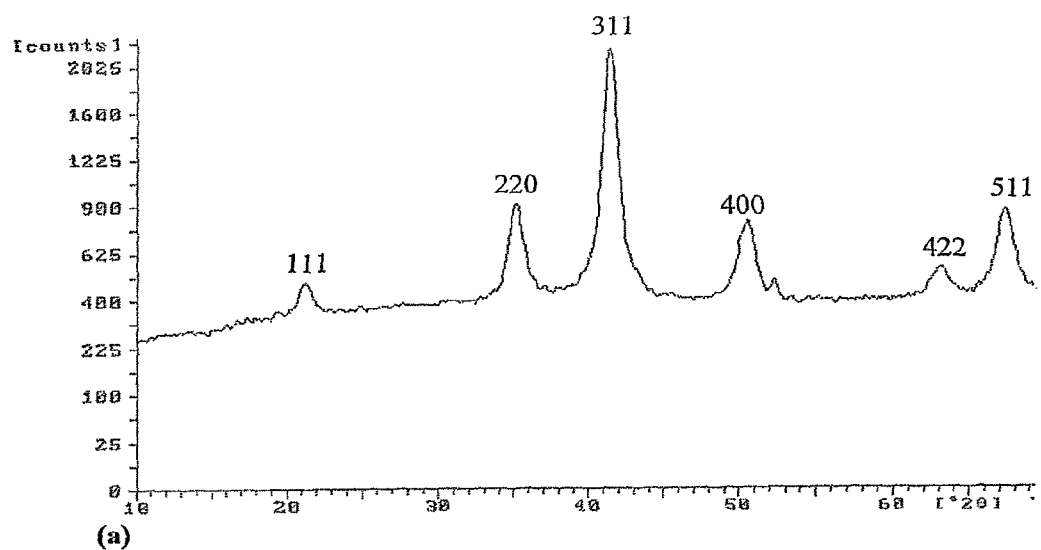
Figure 8:
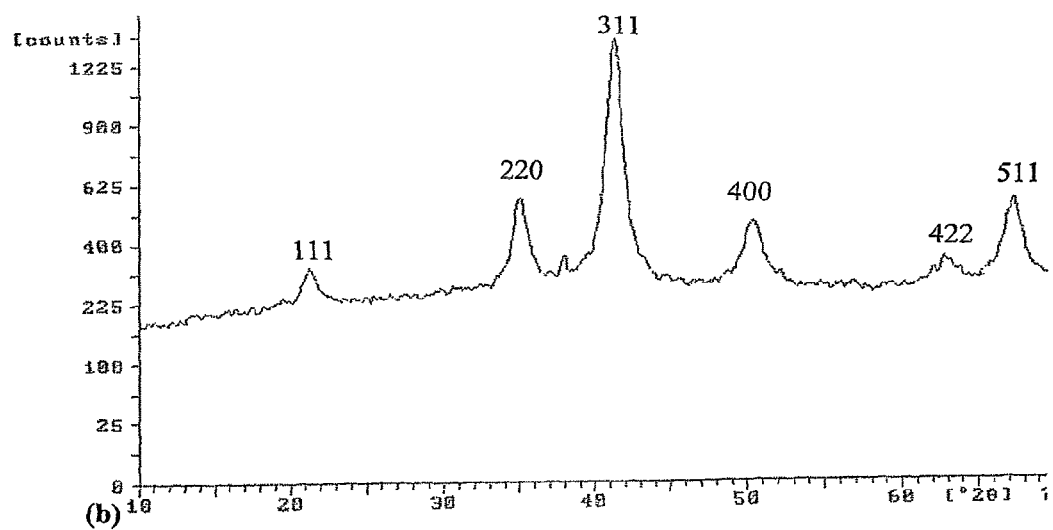

FIG. 8: (a) XRD powder pattern of MNPs.
(b) XRD powder pattern of glyceryl monooleate (GMO) magnetic nanoparticles (MNPs)

Figure 9:
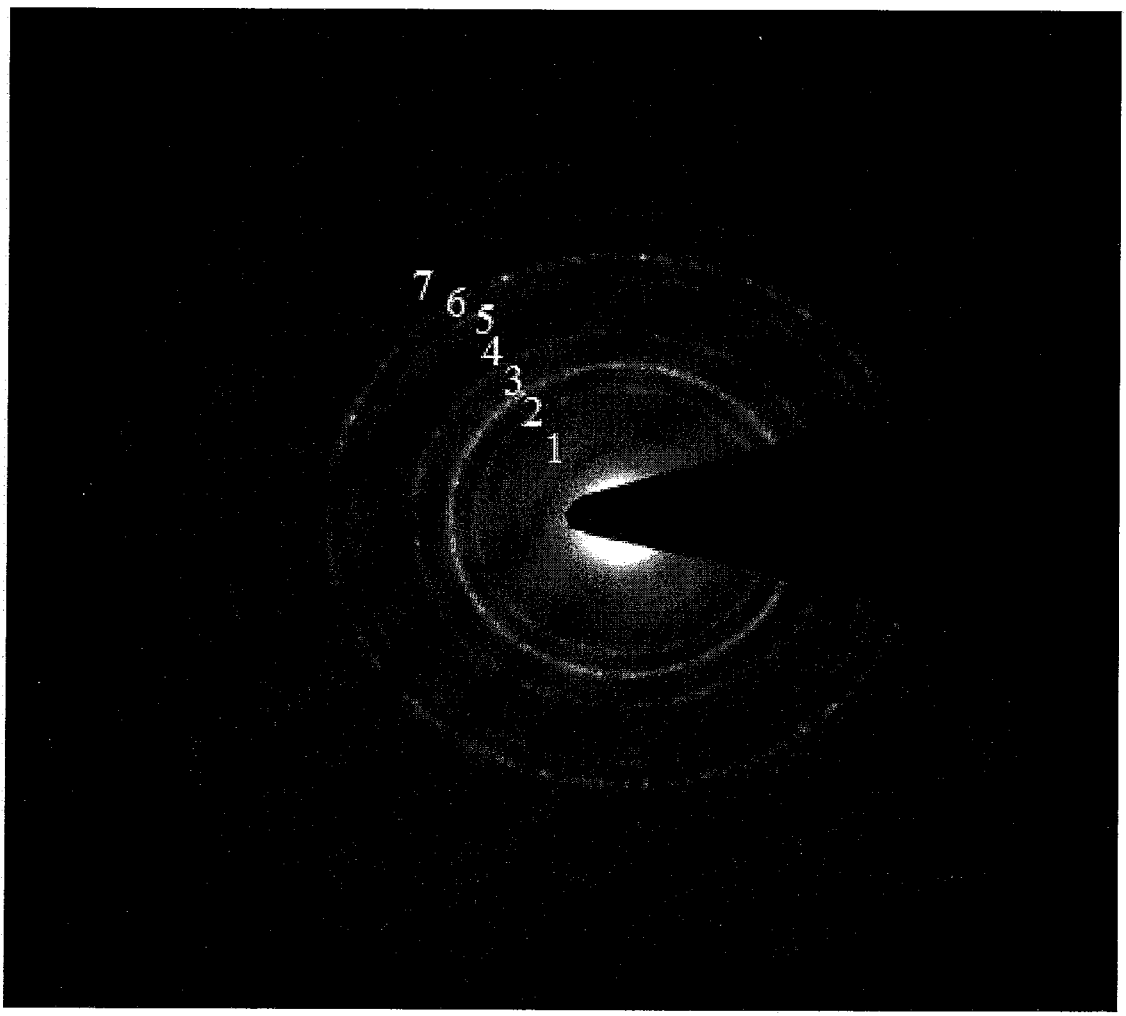

FIG. 9: Selective Area Diffraction (SAD) pattern of native iron oxide showing different rings.

Figure 10:
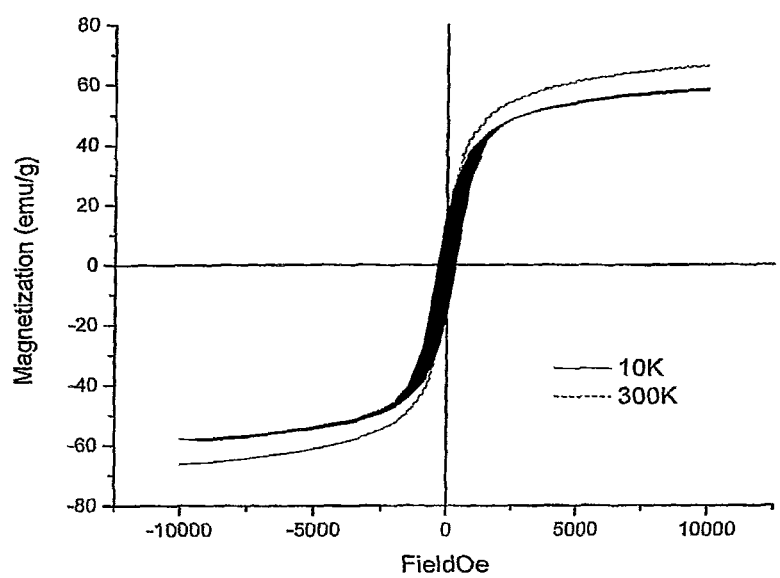
Figure 11:
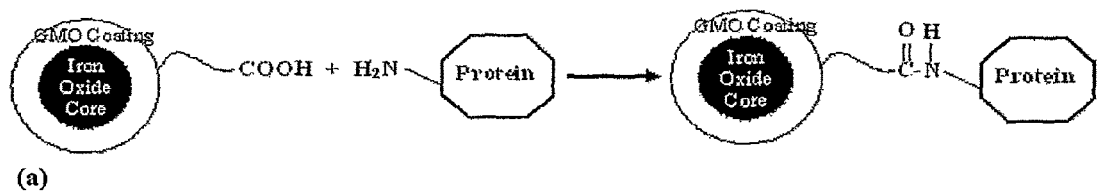
Figure 11:
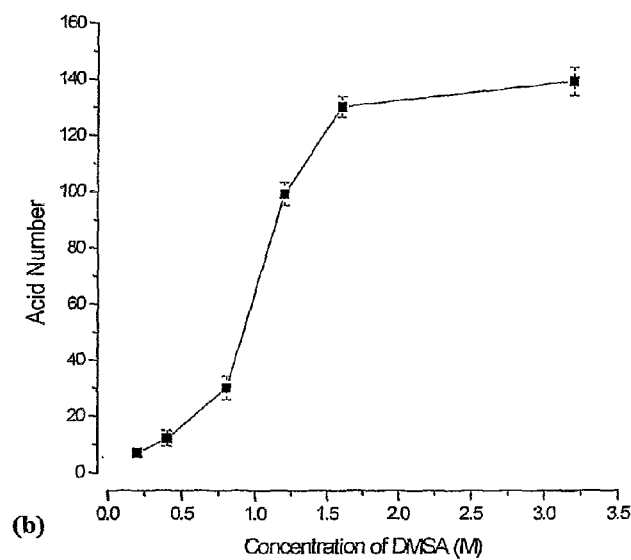

FIG. 10: Magnetization curve of native Iron oxide nanoparticles as a function of field, measured at 10 K and 300 K FIG. 11: (a) Schematic representation of functionalization of glyceryl monooleate (GMO) magnetic nanoparticles (MNPs) with carboxylic groups.
(b) Effect of DMSA concentration on the number of acid groups present per gram of DMSA coated glyceryl monooleate (GMO) magnetic nanoparticles (MNPs).

Figure 12:
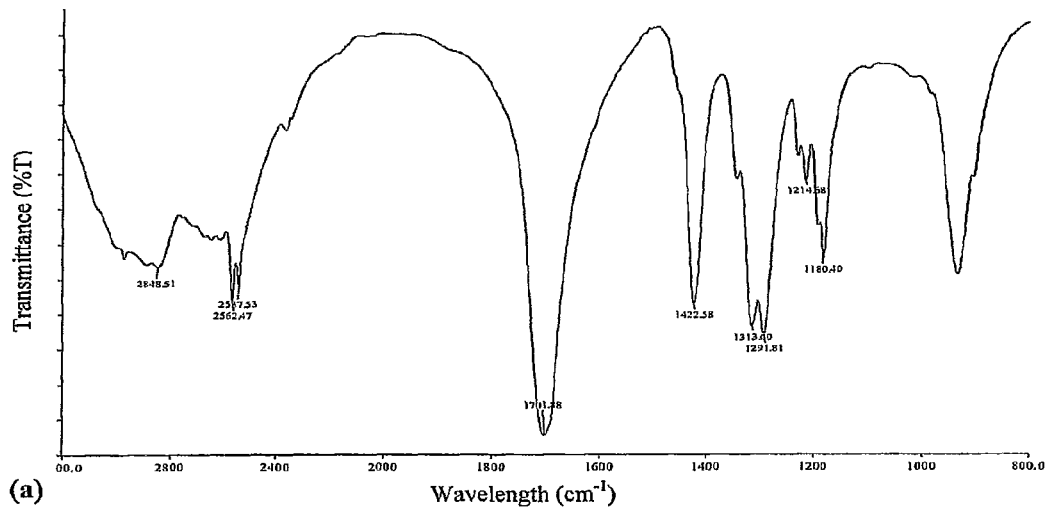
Figure 12:
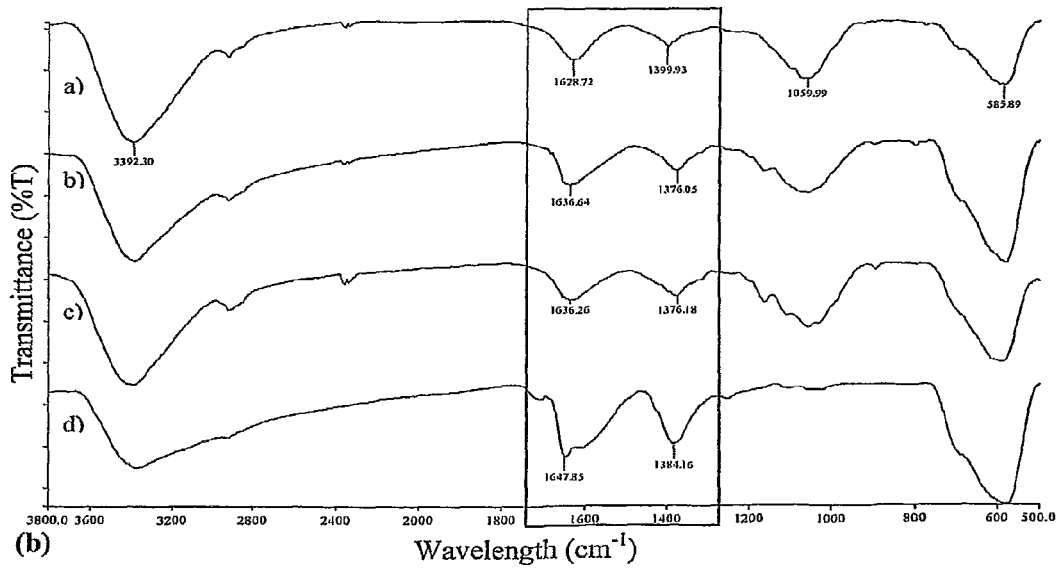

FIG. 12: (a) FT-IR spectra of DMSA.
(b) FT-IR spectra of glyceryl monooleate (GMO) magnetic nanoparticles (MNPs) modified by DMSA:
a) uncoated MNP, b) 0.2 M DMSA, c) 0.4 M DMSA, d) 1.6 M DMSA coated MNP.

Figure 13:
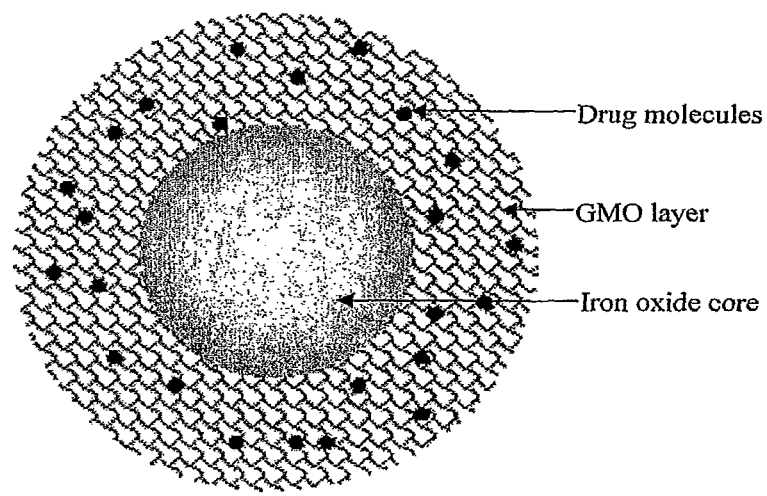

FIG. 13: Schematic representation of drug adsorption in the GMO coating surrounding the iron oxide core.

Figure 14:
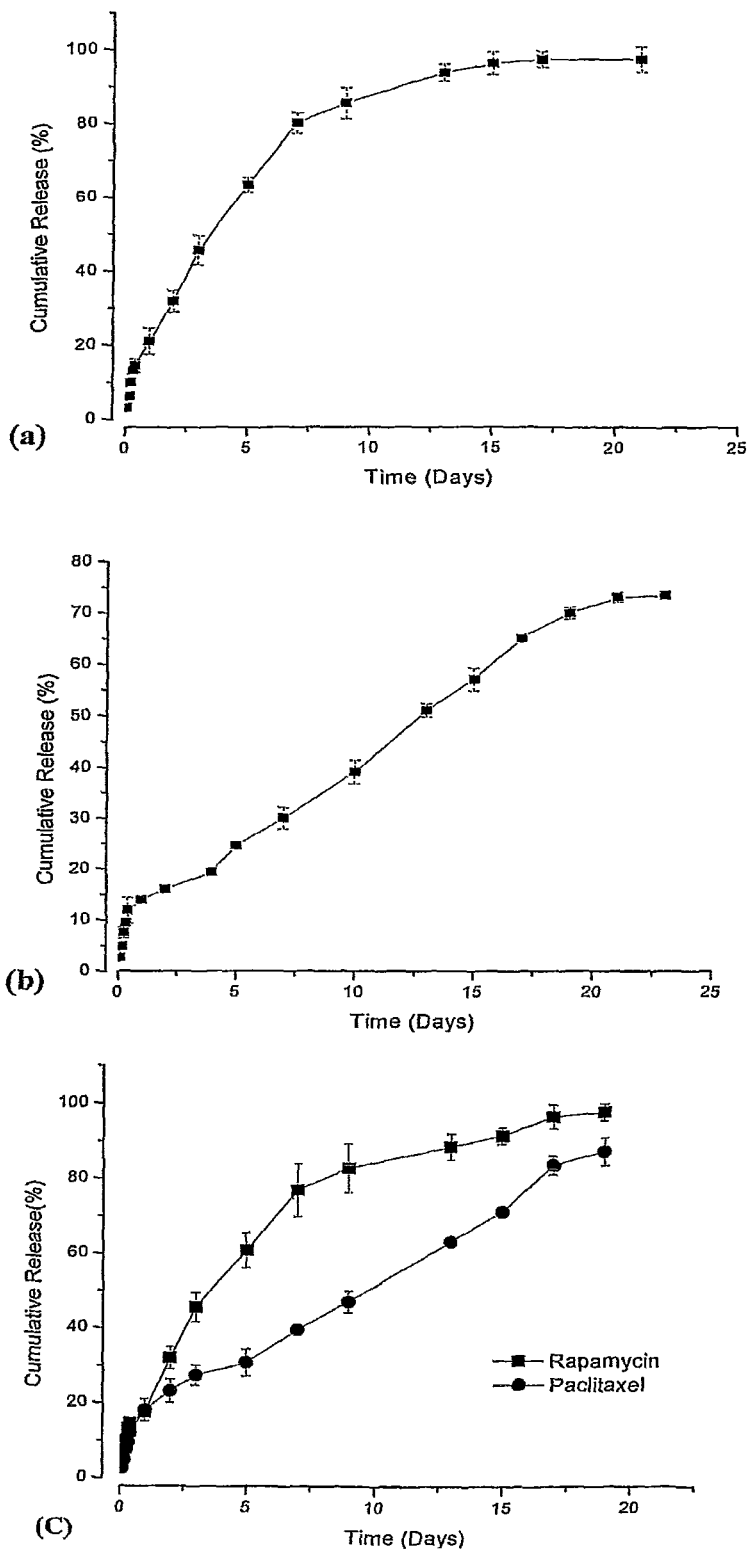

FIG. 14: (a) Release of rapamycin from glyceryl monooleate (GMO) magnetic nanoparticles (MNPs) under in vitro condition. The drug loading in glyceryl monooleate (GMO) magnetic nanoparticles (MNPs) was 7.3% (data as mean±SEM, n=3).
(b) Release of paclitaxel from glyceryl monooleate (GMO) magnetic nanoparticles (MNPs) under in vitro condition. The drug loading in glyceryl monooleate (GMO) magnetic nanoparticles (MNPs) was 7.5%. (Data as mean±SEM, n=3).
(c) Release of paclitaxel and rapamycin from glyceryl monooleate (GMO) magnetic nanoparticles (MNPs) in a combination drug formulation in vitro condition (data as mean±SEM, n=3).

Figure 15:
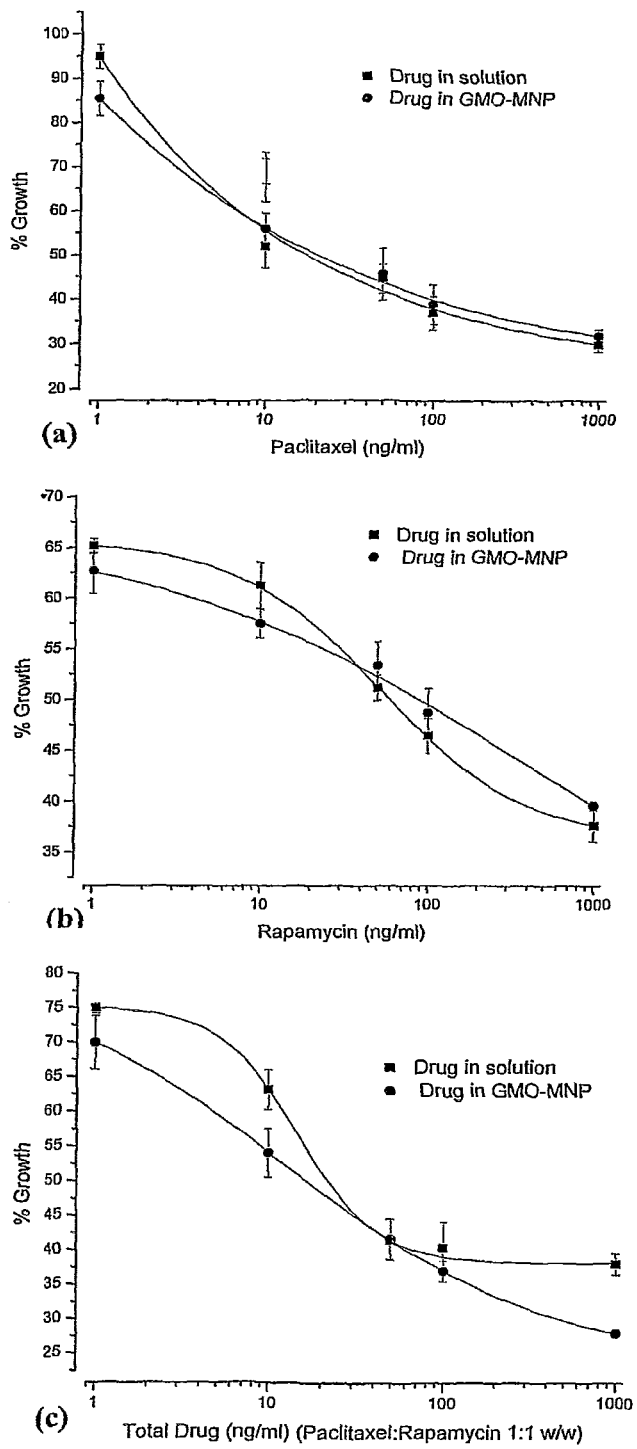

FIG. 15: (a) Antiproiferative effect of drugs in solution and loaded in glyceryl monooleate (GMO) magnetic nanoparticles (MNPs) with paclitaxel in MCF-7 cells. Cells were treated with drug either in solution or in glyceryl monooleate (GMO) magnetic nanoparticles (MNPs), medium was changed on days 2 and 4 and cell viability was measured using MTT assay on day 5 (data as mean±SEM, n=6).
(b) Antiproliferative effect of drugs in solution and loaded in glyceryl monooleate (GMO) magnetic nanoparticles (MNPs) with rapamycin in MCF-7 cells. Cells were treated with drug either in solution or in glyceryl monooleate (GMO) magnetic nanoparticles (MNPs), medium was changed on days, 2 and 4 and cell viability was measured using MTT assay on day 5 (data as mean±SEM, n=6).
(c) Antiproliferative effect of drugs in ablution and loaded in glyceryl monooleate (GMO) magnetic nanoparticles (MNPs) with (paclitaxel+rapamycin) in MCF-7 cells. Cells were treated with drug either in solution or in glyceryl monooleate (GMO) magnetic nanoparticles (MNPs), medium was changed on days 2 and 4 and cell viability was measured using MTT assay on day 5 (data as mean±SEM, n=6).

Figure 16:
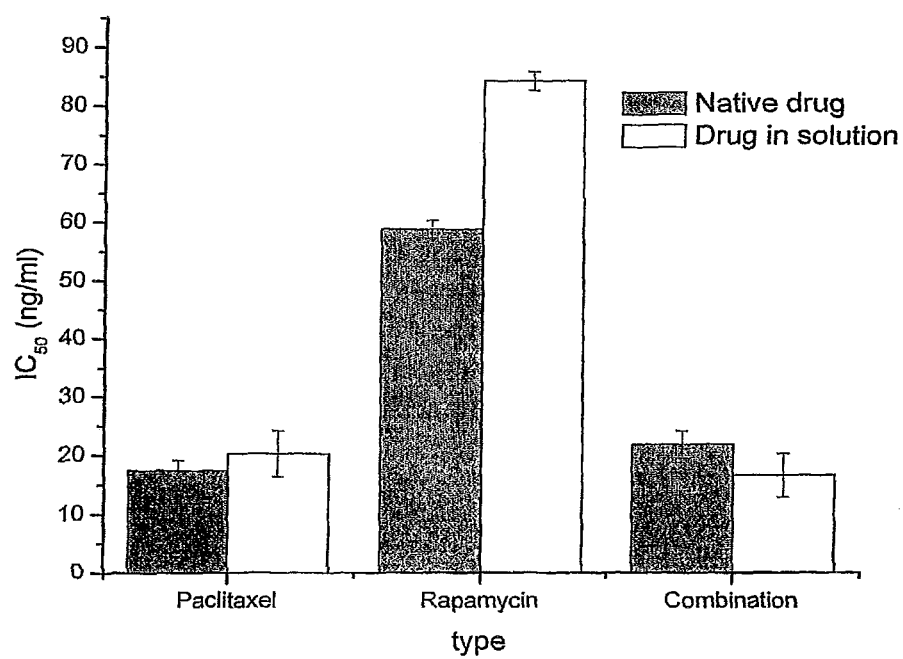

FIG. 16: Antiproliferative effect of hydrophobic drugs in MCF-7 cells: IC Values of paclitaxel, rapamycin and combination of paclitaxel and rapamycin (1:1 w/w ratio) in solution (grey bar) and in glyceryl monooleate (GMO) magnetic nanoparticles (MNPs) (white bar) data as mean±SEM, n=6).

DETAILED DESCRIPTION OF THE INVENTION

Iron (III) chloride hexahydrate ($FeCl_3.6H_2O$) pure granulated, 99%, Iron (II) chloride tetrahydrate ($FeCl_2.4H_2O$) 99%, Ammonium hydroxide, 2, 3 meso mercapto Succinic Acid (DMSA), Tween 80, Pluronic F-127, span series, stannous chloride, mercuric chloride, orthophosphoric acid, potassium dichromate and potassium bromide were purchased from Sigma-Aldrich (St. Louis, Mo.). Glyceryl monooleate was procured from Eastman (Memphis, Tenn.). FITC-BSA (Albumin from Bovine Serum Flurescien conjugated) was procured from Invitrogen Corporation, Carlsbad, Calif., USA. N-(3-Dimethylaminopropyl)-N'-ethyl-Carbomdiimide hydrochloride (EDC) and N-Hydroxy Succinimide (NHS) were procured from Fluka, Sigma Aldrich, Belgium. Barium diphenylamine sulphonate (BDAS) was procured from Acros Organics, Belgium. Paclitaxel, rapamycin were obtained from Shaanxi Schiphar Biotech Pvt Ltd, China.

Magnet NdFeB (12200 G) procured from Edmund Scientific, Tonawada, N.Y.). All other chemical used were of reagent grade obtained from Sigma. MilliQ water purged with nitrogen ($N_2$) gas was used in all steps involved in the synthesis and formulations of magnetic nanoparticles.

Synthesis of Magnetic Nanoparticles.

Synthesis of magnetic particles were done according to the protocol of Jain et al with little modifications. Accordingly, 0.1M Fe (III) (1.35 g $FeCl_3$ dissolved in 50 ml $N_2$ purged water) and 0.1 M Fe (II) (0.99 g $FeCl_2$ dissolved in 50 ml $N_2$ purged water) were prepared. 15 ml of 0.1 M Fe (III) and 7.5 ml 0.1 M Fe (II) were mixed and heated at 80° C. for 10 minutes under constant stirring with a magnetic stirrer in $N_2$ atmosphere. 1.5 ml of ammonium hydroxide (14.5 M) was added to it. Then it was stirred for 20 minutes. Finally the precipitate was washed with $N_2$ purged water with centrifugation at 20,000 rpm for 20 minutes at 10° C. (Sigma centrifuge, 3-16PK, Germany). The pellets were dispersed in 5 ml of MilliQ water and frozen at −80° C. and were lyophilized using a lyophilizer (LABCONCO Corporation, USA) for two days at temperature of −48° C. and 0.05 mbar. The MNP yield was determined by weighing the lyophilized powder and was found to be 110 mg.

Formulations of Magnetic Nanoparticles

Different formulations of iron oxide nanoparticles were developed by the following protocol. 15 ml 0.1 M Fe (III) and 7.5 ml 0.1 M Fe (II) was mixed and heated at 80° C. with constant stirring. 1.5 ml of ammonium hydroxide (14.5 M) was added drop wise to it. Then GMO was added to the suspension drop wise. To study the amount of concentration of GMO required to coat the MNPs, we have prepared different formulations (different weight percentage of GMO to MNP yield were added i.e, 12-560 μl of GMO was added to get 10-504% of GMO coated MNPs). The mixture was allowed to stir for 20 minutes at 80° C. under a $N_2$ atmosphere to evaporate the excess amount of ammonia from the formulation. It was washed with different solvents and centrifugation for 20 minutes at 10° C. at 20,000 rpm (Sigma centrifuge, 3-16PK, Germany). Washing was repeated for three times. The washings of the excess GMO from the magnetic nanoparticles is critical to get a better aqueous dispersibility. To study the effect of different solvent washings on the GMO coated magnetic nanoparticles (GMO-MNPs), different solvents like acetone, ethyl acetate, diethyl ether, chloroform, and mixture of different solvents in different ratio like ethyl acetate:acetone (50:50 and 70:30) were used during the washing steps. The pellets were lyophilized for two days at temperature of −48° C. and 0.05 mbar to get the powder form.

To study the effect of different surfactants on aqueous dispersity of GMO-MNPs, 10 mg of glyceryl monooleate (GMO) Magnetic nanoparticles (MNPs) were taken and dissolved in 10 ml of MilliQ water and was sonicated for 1 minute at 55 watt (VC505, Sonics Vibracell, Sonics and Materials Inc., USA). To this different surfactants were added in the ratio of particle:surfactant (1:1) and was allowed for over night stirring in a closed container to minimize exposure to atmospheric oxygen to prevent oxidation of the MNPs. These particles were washed three times with water to remove the surfactants which were not bounded to the MNPs by magnetic decantation and lyophilized to get the powder fog in for further use.

Characterization of glyceryl monooleate (GMO) Magnetic nanoparticles (MNPs)

Particle size determination by Dynamic Light Scattering and ζ potential Measurements.

Dynamic light scattering (DLS) was used to measure the hydrodynamic diameter and Laser Doppler Anemometry (LDA) was used to determine the zeta potential (mV) of glyceryl monooleate (GMO) Magnetic nanoparticles (MNPs). The DLS and LDA analysis were performed using a Zetasizer Nano ZS (Malvern Instruments, Malvern, UK). The particle size measurement was done by dispersing MNPs (~1 mg/ml) in MilliQ water using water bath sonicator for 1 minute and then the suspension was diluted (100 μl to 1 ml) and the size was measured in polystyerene cuvette using the Zetasizer Nano ZS. To compare the size of the MNPs in organic solvent, the measurement of particle size in n-hexane was made following the same procedure using the quartz cuvette. To further see the effect of size in respect to the different surfactants added to the glyceryl monopleate (GMO) Magnetic nanoparticles (MNPs) (~1 mg/ml) surfactant coated glyceryl monooleate (GMO) Magnetic nanoparticles (MNPs) were suspended in MilliQ water and sonicated using water bath sonicater for 1 minute at 55 watt (VC505, Sonics Vibracell, Sonics and Materials Inc., USA) and further diluted (100 μl to 1 ml) for particle size measurement.

The same suspension in MilliQ water was used for measuring the zeta potential of MNPs.

Transmission Electron Microscopy (TEM).

The internal structure of MNPs were determined by TEM measurements for which a drop of diluted solution of the glyceryl monooleate (GMO) Magnetic nanoparticles (MNPs) (either in water or n-Hexane) was placed in carbon-coated copper TEM grid (150 mesh, Ted Pella Inc, rodding, CA) and was allowed to air-dry. The samples were imaged using a Philips 201 transmission electron microscope (Philips/FEI Inc, Barcliff, Manor, N.Y.). The TEM photograph was taken by using the NIH imaged software. To calculate the mean particle diameter, 50 particles were taken for measurement.

X-ray Diffraction (XRD)

XRD analysis was carried out to know the crystallinity of the MNPs formed. The lyophilized samples (~500 mg) of native iron oxide particles and 100% glyceryl monooleate (GMO) Magnetic nanoparticles (MNPs) were carried out using a Brucker D4 Endeavour, with Bragg-Brentano-Brentano parafocusing geometry. The analysis was done with copper target X-ray tube with Cu Kα radiations. The parameters chosen for the measurement were 2θ steps of 0.08°, 1 second of counting timer per step, and 2θ range from 10.01° to 69.53°.

Determination of Iron content in the magnetic nanoparticle formulations. To determine the percentage of iron present in the MNP formulations, the chemical analysis of the samples was carried out by recommended analytical procedure. Different glyceryl monooleate (GMO) Magnetic nanoparticles (MNPs) formulations (in triplicate) were subjected to di-acid digestion for wet chemical analysis. The MNP formulations (~50 mg) were first digested by adding 2 ml concentrated HCl followed by heating at 60° C. for 10 minutes. Then the digested product was diluted to 25 ml with MilliQ water. To the above diluted sample (5 ml); 2 ml of concentrated HCl was added and heated at 60° C. for 10 minutes. 4 ml of 0.25 M stannous chloride was added drop wise to the digested product up to decolouration. Then the sample was cooled to room temperature and 2 ml of saturated mercuric chloride was added and was mixed well by shaking. To the mixture, 10 ml of Zimmerman-Reinhard reagent (5 ml Of 5% sulphuric acid and 5 ml of orthophosphoric acid) was added followed by addition of 10 ml of MilliQ water. Finally, the iron content in the formulation was analyzed volumetrically by titrating against 0.01N potassium dichromate solution using barium diphenylamine sulfonate (BDAS) indicator.

Fourier Transform Infrared Spectroscopy (FT-IR).

FT-IR measurement was carried out to know the chemical interactions in the MNP formulations. FT-IR (Perkin Elmer, FTIR Spectrometer, SPECTRUM RX 1) was used to characterize the surface composition of the different formulations of MNPs. Each spectrum was obtained by averaging 32 interferograms with resolution of 2 cm$^{-1}$ in the range of 400 to 4000 cm$^{-1}$. A small amount of MNPs (either native or formulated) were milled with KBr, and a mixture of them was pressed into a pellet for analysis with a pressure of 150 kg/cm$^2$.

Magnetization Studies

In order to quantify the amount of magnetism present in the formulated MNPs magnetization study was carried. The Magnetic properties were investigated by a Superconducting Quantum Interference Device (SQUID) magnetometer (MPMS5, Qunatum Design) with fields up to 1.5 T and temperatures of 10 K and 300 K respectively. Zero-field-cooled (ZFC) and field-cooled (FC) magnetization measurements were, carried out as a function of temperature. To determine the ZFC measurements the samples were cooled from 300 K to 10 K in zero fields as a function of temperature at 100 Oe field strength as gradually warmed. To take the FC measurement, the sample as cooled in the measuring field. The magnetization was determined as a function of field M (H) at 10 and 300 K. By, putting the magnetization curve in an analytical ferromagnetic model and by normalizing the diamagnetic contribution (x) due to the background the saturation magnetization (Ms) and the Coercive field (Hc) were determined.

Loading of Anticancer Drugs in Magnetic Nanoparticles.

To exploit the MNP formulations as a drug delivery vehicle, anticancer drugs were taken into account. For the incorporation of anticancer drugs in glyceryl monooleate (GMO) Magnetic nanoparticles (MNPs), paclitaxel, rapamycin and a combination of both (paclitaxel and rapamycin) were used. We have used 100% GMO coated MNPs for drug loading. 100 mg of the glyceryl monooleate (GMO) Magnetic nanoparticles (MNPs) were dispersed in 10 ml MilliQ water and was sonicated for 1 minute. The drugs were dissolved in organic solvent acetonitrile either individually or in combination (10% w/w to the polymer i.e, 10 mg of either of the drugs dissolved in 1 ml or 1 ml of combined drugs, 5 mg each). The drug was added drop wise to the glyceryl monooleate (GMO) Magnetic nanoparticles (MNPs) suspension and kept for overnight stirring with a magnetic stirrer to allow the partitioning of the drug into the GMO shells surrounding the magnetic nanoparticles. The un-partitioned drugs were washed with water and were separated by centrifuging the particle suspension at 13, 800 rpm for 10 minutes at 10° C. (Sigma centrifuge, 3-16PK, Germany). Washing was repeated for three times for the complete removal of the un-entrapped drug. The pellets were lyophilized for quantification of entrapment efficiency of different drugs through reverse phase high performance liquid chromatography (RP-HPLC).

Quantification of Drug by RP-HPLC

Quantification of the drug incorporated in the MNPs, was carried out through RP-HPLC. The estimation of the amount of drug entrapped in the glyceryl monooleate (GMO) Magnetic nanoparticles (MNPs) was done by direct method. To the lyophilized nanoparticles solvent acetonitrile (1 mg/ml) was added and sonicated in an ice bath for 1 minute, at 55 watt and kept in shaker for 24 hours for the drug to come out from the particles. Then the nanoparticles were centrifuged for 10 minutes at 13, 800 rpm at 10° C. (Sigma microcentrifuge, 1-15PK, Germany).

Supernatants were taken out for the estimation of drug entrapped. The analysis of sample was done by reverse phase isocratic mode of HPLC with little modification using Agilent 1100 (Agilent technologies, Waldbronn Analytical Division, Germany) which consists of a column (Zorbax Eclipse XDB-C18, 150×4.6 mm, i.d). 20 µl of different drug samples were injected manually in the injection port and were analyzed with the mobile phase of acetonitrile:water 180:20 v/v), which was delivered at flow rate of 1 ml/min with a quaternary pump (Model. No—G1311A) at 25° C. with thermostat (Model No—G1316A). The drug levels were quantified by UV detection at 228 nm for paclitaxel and 278 nm for rapamycin with a detector (DAD, Model—G 1315A). The amount of drug (paclitaxel and rapamycin) in samples was determined from the peak area correlated with the standard curve. The standard curves of paclitaxel and of rapamycin were prepared under identical conditions. The entrapment efficiency was calculated from the following formula reported earlier.

% of Entrapment Efficiency=(drug loaded in nanoparticles/drug added in formulation)×100

Kinetics of Paclitaxel and Rapamycin Release from Magnetic Nanoparticles.

To know the amount of drug released in in vitro condition a kinetics Measurement was done. The release of drugs from glyceryl monooleate (GMO) Magnetic nanoparticles (MNPs) was carried out by dissolving 10 mg of nanoparticles in 3 ml of PBS (pH=7.4, 0.01 M, containing 0.1% w/v of Tween 80). Tween 80 was used in the buffer to maintain the sink condition during the release study. It was mixed properly by vortexing and then was divided into three parts, 1 ml each. All the samples were kept in an orbit shaking incubator (Wadegati Labequip, India) at 37° C., rotating at 150 rpm. The samples were removed at predetermined time intervals and centrifuged at 13, 800 rpm for 15 minutes at 10° C. (Sigma microcentrifuge, 1-15 PK, Germany) to get the supernatant. Then the pellets were dispersed with the same volume of fresh PBS (pH=7.4, 0.01 M PBS, containing 0.1% w/v of Tween 80) and vortexed and kept in shaker. The collected supernatants were lyophilized for 48 hours, and then were dissolved in acetonitrile and centrifuged at 13, 800 rpm for 10 minutes at 4° C. (Sigma microcentrifuge, 1-15PK, Germany). The obtained supernatant was taken out and injected in the RP-HPLC to determine the amount of drug released either paclitaxel, rapamycin or combination of both with respect to different time intervals:

Cell Culture

The cell culture experiments were carried out in MCF-7 (breast cancer) cell line purchased from American Type Culture Collection (ATCC, Manassas, Va.) were grown in RPMI 1640 medium (Himedia Laboratories Pvt. Ltd., Mumbai, India) supplemented with 10% fetal bovine serum (Himedia Laboratories Pvt. Ltd., Mumbai, India) and 100 µg/ml penicillin G and 100 µg/ml streptomycin (Gibco BRL, Grand island, NY) at 37° C. in a humidified and 5% CO$_2$ atmosphere (Hera Cell, Thermo Scientific, Waltham, Mass.).

Statistical Analysis

Statistical analyses were performed using a Student's t test. The differences were considered significant for p values of <0.05.

Mitogenic Assay.

To find out the cytotoxicity of the anticancer drugs, mitogenic assay was carried out. The MCF-7 cells were seeded at 5,000 per well in 96 well plate (Corning, N.Y., USA) and kept in the incubator for 24 hours for better cell attachment. Different concentrations of paclitaxel, rapamycin or combination of the drug (0.1 µM to 1000 µM), either in solution or loaded in glyceryl monooleate (GMO) Magnetic nanoparticles (MNPs) were added. Glyceryl monooleate (GMO) Magnetic nanoparticles (MNPs) without drug and medium were used as respective controls. The medium was changed on $2^{nd}$ and $4^{th}$ days following the drug treatment; no further dose of drug was added. Viability of the cells was determined at $5^{th}$ day. After the specified incubation time, 10 µl MTT (Sigma) was added, and the plates were incubated for 3 hours at 37° C. in a cell culture incubator (Hera Cell, Thermo Scientific, Waltham, Mass.), following which the intracellular formazan crystals were solubilized in dimethyl sulfoxide and the color intensity was measured at 540 nm using a microplate reader (Synergy HT, BioTek Instruments, Inc., Winooski, Vt.). The antiproliferative effect of different treatments was calculated as a percentage of cell growth with respect to respective controls.

Surface Functionalization of Magnetic Nanoparticles

MNPs are difficult to bond with biomolecules in aqueous solution. Therefore, to attach any biomolecule on to the surface of the MNPs, the surface should be functionalized with different functional groups like carboxylic or amine group. To attach any peptide or protein on to the surface of the MNPs, the particles should be surface functionalized with carboxylic groups. Therefore, 2, 3 meso mercapto succinic acid (DMSA) was used to functionalize the glyceryl monooleate (GMO) Magnetic nanoparticles (MNPs) with carboxylic acid groups. 500 mg of glyceryl monooleate (GMO) Magnetic nanoparticles (MNPs) was added to 5 ml of 0.2 M DMSA dissolved, in DMF and kept for 24 hours stirring in a magnetic stirrer. The sample was washed with ethanol three times by centrifuging at 13,800 rpm at 10° C. for 20 minutes and the pellets were lyophilized. To find out the effect of DMSA in the functionalization of glyceryl monooleate (GMO) Magnetic nanoparticles (MNPs), we have used different concentrations of DMSA solutions (0.4-3.2 M) and followed the above procedure to get the lyophilized powder.

Acid Number Determination.

For the quantification of free carboxylic acid groups attached on the surface of MNPs, acid numbers of the glyceryl monooleate (GMO) Magnetic nanoparticles (MNPs) were determined by the experimental protocol 20 mg of the different concentration of DMSA coated glyceryl monooleate (GMO) Magnetic nanoparticles (MNPs) were initially treated with 5 ml NaOH (1 N) for 30 minutes to cleave some of the surface ester bonds to generate free carboxylic ends. Then the samples were washed three times with MilliQ water by centrifuging at 13,800 rpm at 10° C. for 20 minutes. Then all the samples were vacuum dried by lyophilizes. Free acid groups present on the glyceryl monooleate (GMO) Magnetic nanoparticles (MNPs) surface were quantified by taking nanoparticle solution 1 mg/ml and diluting to 50 times. Then the diluted solution was titrated against NaOH (0.0005 N). NaOH solution is to be standardized before by titrating against oxalic acid. Acid number was calculated by the following formula.

nanoparticles (MNPs) were added to 5 ml of PBS (pH=7.4, 0.02 M). 250 µl of EDC and 250 µl of NHS in PBS (pH=7.4, 0.02 M, 1 mg/ml) was added to it. The sample was left in room temperature under magnetic stirring for 4 hours. Then the sample was magnetically decanted to remove free EDC and NHS. To the pellet 3 ml of PBS (pH=7.4, 0.02 M) and 100 µl of FITC-BSA (1 mg/ml) was added. The solution was left for 2 hours and then incubated at 4° C. overnight. Next day magnetic decantation was done and the pellets were washed two times with PBS (pH=7.4, 0.02 M) to remove any unconjugated FITC-BSA. A standard plot for FITC-BSA was prepared taking concentrations 2.5-20 µg/ml at $\lambda_{ex}$=488 nm and $\lambda_{em}$=520 nm using a fluorescence microplate reader (Synergy HT, BioTek Instruments, Inc., Winooski, Vt.). The percentage of conjugation of FITC-BSA to the glyceryl monooleate (GMO) Magnetic nanoparticles (MNPs) was calculated by indirect method. First, the amount of un-conjugated FITC-BSA present in the supernatant was determined by taking the fluorescence measurement and using the standard plot of FITC-BSA. Then the amount of un-conjugated FITC-BSA was deducted from the total FITC-BSA amount added to get the amount of conjugated FITC-BSA.

Physical Characterization of Magnetic Nanoparticles (MNPs).

Due to the hydrophilicity nature of the native iron oxide particles, they preclude dispersibility in organic solvents. During coating of GMO to the magnetic nanoparticles, GMO gets chemisorbed on the surface of the iron oxide particles. The hydrophobic nature of the GMO makes the GMO coated magnetic particles easily dispersible in the organic solvents. The use of nanoparticles for the drug delivery purpose, it is better to have a water dispersible formulation. For getting a good water dispersible formulation, excess amount of GMO has to be washed off from the surface of the MNPs. Therefore different organic solvents like acetone, ethyl acetate, diethyl ether, chloroform, and mixture of different solvents in different ratio like ethyl acetate:acetone (50:50 and 70:30) was tried as the washing solvent. These solvents were used for washing during the centrifugation to remove the excess un-adsorbed coating from the surface of iron oxide particles. It has been found that when acetone, diethylether, ethylacetate and chloroform were used alone as the washing solvent during the processing of the MNPs, the resulted nanoparticles were having a considerable size of around 130 nm in organic solvent but they posses a higher size range and poor dispersibility in water (FIG. 1). Therefore a combination of two organic solvents i.e, ethyl acetate and acetone (having inter miscibility behavior) with varying ratios (50:50 and 70:30 v/v) were employed in the washing steps to remove the excess amount of GMO. It has been found that with washing in ethyl acetate: acetone (70:30 v/v), the resulted MNPs were with good particle diameter around 144 nm (FIG. 1 and Table 1) and also having better water dispersibility (FIG. 2c). Therefore further works were carried out with a mixture of ethyl acetate and acetone in 70:30 v/v ratios. Both ethyl acetate and acetone are dipolar aprotic solvents. They help to remove the $$A = \frac{\text{Volume required during titration} * \text{Normality of NaOH} * 40 \text{ (Mol. Wt. of NaOH)}}{\text{Weight of nanoparticles (g)}}$$

Conjugation of FITC-BSA

FITC BSA was conjugated to the carboxyl groups, which were functionalized on the surface of glyceryl monooleate (GMO) Magnetic nanoparticles (MNPs). For conjugation, 10 mg of functionalized glyceryl monooleate (GMO) Magnetic excess hydrophobic coating from the magnetic nanoparticle surface. This in turn results in better, aqueous dispersibility.

For the absolute covering of iron oxide nanoparticles with GMO, it is very much critical to know the optimum percentage of coating for their eventual dispersion in hexane or water.

Particles were prepared with an increase in GMO concentration (of the total formulation content). With an increase in GMO concentration there is less particle sedimentation and good dispersibility in water (FIG. 2a) giving the MNPs a better colloidal stability up to around one month (FIG. 2a). With the increase in GMO concentration, the obtained glyceryl monooleate (GMO) Magnetic nanoparticles (MNPs) gives narrow range of particle diameter both in water and hexane (FIG. 3b). Thus our experimental outcomes reveal that the GMO coating on the surface of the iron oxide particles is required to give stable liquid crystals.

FTIR

To analyze the surface chemistry of the native MNP and glyceryl monooleate (GMO) Magnetic nanoparticles (MNPs), the FT-IR measurements of the nanoparticles were taken and shown in (FIG. 4a). The spectra of pure GMO shows the peaks at 1730 cm$^{-1}$, 3400 cm$^{-1}$ and 2937 cm$^{-1}$ which corresponds to the ester bond, O—H stretch dimmer H bonded and $CH_2$ stretching modes respectively. The spectra of GMO coated iron oxide nanoparticles shows absence of the ester bond C=O stretch present at 1730 cm$^{-1}$. This suggests the adsorption of ester group of GMO onto the surface of nanoparticles. Further, in the coated particles, the vibrational stretch of COO— at 1400 cm$^{-1}$ gradually increases with increase in percentage of GMO. Also, a band at 1166 cm$^{-1}$ due to the absorbance of C—O stretch gradually increases with increase in concentration of GMO. This finding indicates that the ester group is chemisorbed onto the surface in carboxylated form with oxygen atom coordinated to the nanoparticle surface (FIG. 4f). These results reveal significance of surface interaction between GMO and the iron oxide nanoparticle surface for preparation of magnetic nanoparticles completely coated with GMO. The strong IR band at 584 cm$^{-1}$ is the characteristic of the Fe—O vibration found in the native MNPs. After coating of GMO to the MNPs the peak of Fe—O slightly shifts to ~592 cm$^{-1}$. Furthermore, the appropriate amount of, GMO required for steric stabilization of the nanoparticles was also investigated. The (FIG. 4b) represents the infrared spectra of iron oxide nanoparticles coated with different concentrations of GMO. The peak at around 1165 cm$^{-1}$ (FIG. 4e) corresponding to C—O stretch starts to appear for concentrations of GMO more than 15% used in the formulation. Furthermore, as the GMO concentration increases, the intensity of asymmetric $CH_2$ stretch at 2922 cm$^{-1}$ (FIG. 4d) and C—H deformation vibration at 1056 cm$^{-1}$ (FIG. 4e) increases. Also, the intensity of OH vibration band at around 3400 cm$^{-1}$ (FIG. 4c) gets broader as the GMO concentration increases.

Further, to know the role of surfactant over the aqueous dispersibility of the GMO-MNPs, various range of surfactants such as pluronic (F-127) and Span series (80, 20, 85, 60, 65) were tested (FIG. 5a). The effect of different surfactants on the aqueous dispersibility of the coated magnetic nanoparticles revealed that Span 65 gives the best water dispersibility with particle size about 148 nm (FIG. 5b). But if we will compare the size of native glyceryl monooleate (GMO) Magnetic nanoparticle (MNP) and glyceryl monooleate (GMO) Magnetic nanoparticle (MNP) with span 65 there is no significant change (FIG. 6). So the result revealed that the GMO coated MNPs give a better water dispersibility and better particle size even in the absence of any surfactant. The shape, size, and uniformity of the particles were also determined by TEM images. The picture shown in (FIG. 7a) shows that the particles are shaped spherically and monodispersed with a size of below 10 nm. In hexane also the glyceryl monooleate (GMO) Magnetic nanoparticles (MNPs) show spherical shape with monodispersibility (FIG. 7b). A statistical analysis of the size of GMO coated MNP population varies from 6 nm to 11 nm with a mode value of 7 nm (FIG. 7c). The particle size measured by TEM is less than that measured by laser light scattering because, laser light scattering measures the hydrodynamic diameter where there is some aggregation of the MNPs.

X-ray diffraction analysis is a technique which reveals information about the crystallographic structure, chemical composition, and physical properties of materials. X-ray diffraction patterns of the native iron oxide particles revealed diffraction peaks at 110, 220, 311, 400, 422 and 511 which are the characteristic peaks of the $Fe_3O_4$ crystal with a cubic spinel structure. The position and relative intensity of all diffraction peaks were identical with standard spectra of magnetite. Here, no peaks corresponding to $\gamma$-$Fe_2O_3$ and $\alpha$ $Fe_2O_3$ like 210, 213 etc are observed. This suggests that there are no impurities like a ferric oxide in the glyceryl monooleate (GMO) Magnetic nanoparticle (MNP) formulations. The XRD pattern of GMO coated MNP showed the same peaks at the same position, but, the intensity of the magnetite peak at 311 is less than that of native iron oxide particle (FIGS. 8a and 8b). This lowering of intensity of the magnetite peak is due to the GMO coat over the MNP surface. The rings in the selected Area Diffraction (SAD) image shown in (FIG. 9) were consistent with a cubic inverse spinal structure of magnetite and it indicates the good crystallinity of the nanoparticles. The characteristic d spacing corresponds to the hkl values, {111}, {220}, {311}, {400}, {422}, {511}. These results showed a good coincidence with the XRD data. The SAD values also correspond to the standard atomic spacing for $Fe_3O_4$ along with respective hkl indexes from the Joint Committee on Powder Diffraction Standards (JCPDS) card number (19-0629) (Table 2).

Iron Content Analysis

The iron content in the formulated glyceryl monooleate (GMO) Magnetic nanoparticles (MNPs) must be sufficient to respond to an external magnetic field. Therefore the amount of iron content in the nanoparticles was determined. The determination of iron content in the GMO coated magnetic nanoparticles revealed that the iron content in native iron oxide particles was found to be 70.37%. Iron content in 100% w/w glyceryl monooleate (GMO) Magnetic nanoparticles (MNPs) was found to be 67.57%. When the percentage of GMO was increased to 504% w/w the iron content in the nanoparticles was decreased to 63.11%.

Squid

The saturation magnetization Ms at 10 K and 300 K and the coercivity Hc of native MNPS and glyceryl monooleate (GMO) Magnetic nanoparticles (MNPs) are shown in (Table 3). The Ms values were normalized assuming 100% magnetite for the simplicity using iron mass. The SQUID analysis shows typical hysteresis curves at 10 and 300 K for the optimized nanoparticles formulation as depicted in (FIG. 10). The hysteresis loop have negligible coercivity at room temperature, and the magnetization at 1.5 T (after subtracting the diamagnetic background) were 50.4±0.3 emu/$g_{magnetite}$ for 504% glyceryl monooleate (GMO) Magnetic nanoparticles (MNPs), 52.2±0.7 emu/$g_{magnetite}$ for 100% glyceryl monooleate (GMO) Magnetic nanoparticles (MNPs) and 63.73±0.7 emu/$g_{magnetite}$ for uncoated MNPs at 300 K. The nanoparticles were not superparamagnetic at 10 K. The saturation magnetization at 10 K for glyceryl monooleate (GMO) Magnetic nanoparticles (MNPs) were higher than that of uncoated MNPs and hysteresis developed. From the magnetization values it can be measured that 100% w/w glyceryl monooleate (GMO) Magnetic nanoparticle (MNP) has actually only 18.0% w/w GMO coating where as 504% w/w glyceryl monooleate (GMO) Magnetic nanoparticle (MNP) has only 20.4% w/w GMO on the surface.

Functionalization and Characterization of MNPs.

The most unique feature of magnetic nanoparticles is their response to a magnetic force (FIG. 2b), and this feature has been utilized in applications such as drug targeting and bioseparation including cell sorting. Since magnetic nanoparticles are attracted to a high magnetic flux density, it is possible to manipulate cells labeled with magnetic nanoparticles using external magnets. To make the magnetic nanoparticles usable for cell sorting or bioseparation purpose first the particle should be functionalized through a coating or encapsulation of specific chemical group or charge because the MNPs are difficult to bond directly with biomolecules in an aqueous solution. To attach any biomolecule like peptide or protein or any primary amine on to the surface of the magnetic nanoparticles, the particles should be surface functionalized with carboxylic group or amine groups. In this study, we have functionalized —COOH groups on to the surface of the glyceryl monooleate (GMO) Magnetic nanoparticles (MNPs) (FIG. 11a). The functionalization of magnetic nanoparticles with carboxylic group was achieved by coating with DMSA which was confirmed by FTIR and acid number determination from the nanoparticles.

In the FTIR spectra of pure DMSA (FIG. 12a), the peak at 1701 $cm^{-1}$ corresponds to C=O stretch. The peaks around 2550 $cm^{-1}$ and 3850 $cm^{-1}$ corresponds to the S—H stretch and OH stretch respectively. The (FIG. 12b) depicts that the uncoated glyceryl monooleate (GMO) Magnetic nanoparticle (MNP) and the DMSA coated glyceryl monooleate (GMO) Magnetic nanoparticles (MNPs) have a strong absorbance of Fe—O bond at around 580 $cm^{-1}$ and absorbance of O—H stretch at around 3400 $cm^{-1}$. After coating of DMSA to the glyceryl monooleate (GMO) Magnetic nanoparticles (MNPs), the peak at 1701 $cm^{-1}$ corresponding to C=O stretch in pure DMSA can be located in DMSA coated glyceryl monooleate (GMO) Magnetic nanoparticles (MNPs) with a shift to around 1650 $cm^{-1}$ and the intensity increases as we go on increasing the concentration of DMSA from 0.2 to 1.6 M; Another vibrational mode at around 1376 $cm^{-1}$ is assigned to C—O stretch which also increases with increase in concentration of DMSA. So the FTIR data suggests the attachment of carboxylic group to the surface of the glyceryl monooleate (GMO) Magnetic nanoparticles (MNPs). The attachment of carboxylic groups on to the surface of the glyceryl monooleate (GMO) Magnetic nanoparticles (MNPs) can also be confirmed by chemical analysis through acid number determination by acid base titration method. Acid number is an important parameter to quantify the free carboxylic acid groups present on the surface of the MNPs. The (FIG. 11b) shows the effect of concentration of, DMSA on the acid number of the MNPs. There is an increase of acid number from 8 to 130/gm of MNPs with an increase of concentration of DMSA from 0.2 M to 1.6 M. But further increase in concentration of DMSA does not significantly change the acid number, which shows a saturation binding of DMSA on the MNPs surface. Therefore, glyceryl monooleate (GMO) Magnetic nanoparticles (MNPs) with 1.6 M DMSA coating were selected for further experiments.

FITC-BSA was taken as a model protein to determine the efficacy of the carboxylic group functionalized glyceryl monooleate (GMO) Magnetic nanoparticles (MNPs). The conjugation of FITC-BSA was done to the glyceryl monooleate (GMO) Magnetic nanoparticles (MNPs) coated with 1.6 M DMSA. The conjugation efficiency was calculated by taking the absorbance at $\lambda_{ex}$=488 nm and $\lambda_{em}$=520 nm using a fluorescence microplate reader. It was found that with addition of 100 μg of FITC BSA to 10 mg of magnetic nanoparticles; about 91% of FITC-BSA was conjugated.

Characterization of Drug Loaded MNPs

The mean hydrodynamic diameter of the formulated glyceryl monooleate (GMO) Magnetic nanoparticles (MNPs) with and without drugs was found to be in the range of 150-200 nm with a polydispersity index (PI) of ~0.2 (Table 4). The zeta potential is another important parameter to know the stability of the MNP formulations. It measures the magnitude of the repulsion and attraction between the particles. The zeta potential of glyceryl monooleate (GMO) Magnetic nanoparticles (MNPs) was found to be ~36 mV. Incorporation of drugs showed a decrease in zeta potential of the glyceryl monooleate (GMO) Magnetic nanoparticles (MNPs) to 22-26 mV as depicted in (Table 4). But the overall high positive zeta potential of ~30 mV shows the stability of the different glyceryl monooleate (GMO) Magnetic nanoparticle (MNP) formulations. The amount of drugs incorporated in the glyceryl monooleate (GMO) Magnetic nanoparticles (MNPs) was quantified by measuring the encapsulation efficiency. Paclitaxel loading in glyceryl monooleate (GMO) Magnetic nanoparticles (MNPs) showed an encapsulation efficiency of 75% (i.e, 75% of the added drug was entrapped in the formulation). Similarly, rapamycin loaded glyceryl monooleate (GMO) Magnetic nanoparticles (MNPs) showed an encapsulation efficiency of 73% (i.e, 73% of the added drug was entrapped in the formulation). When both the drugs were used in the glyceryl monooleate (GMO) Magnetic nanoparticle (MNP) formulation, 0.25 encapsulation efficiency of paclitaxel was 98% and rapamycin was 99%. A sustained release of the drugs was observed from the in vitro release profiles (FIG. 14). The release of paclitaxel and rapamycin from the glyceryl monooleate (GMO) Magnetic nanoparticles (MNPs) was 73%, 80% respectively in two weeks showing a sustained release profile. In the combined drug formulation (paclitaxel+rapamycin), the release of rapamycin drug was around 91% in two weeks whereas the release of paclitaxel was around 81%.

Antiproliferative Activity of Drug Loaded Glyceryl Monooleate (GMO) Magnetic Nanoparticles (MNPs)

The Cell viability percentage due to the different drug loaded glyceryl monooleate (GMO) Magnetic nanoparticle (MNP) formulations were determined by MIT assay. The result showed the typical dose dependent sigmoidal antiproliferative effect on the MCF-7 cells. As the concentration of paclitaxel was increased from 1 ng to 1000 ng/ml the cell viability percentage decreased from 95% to about 30% in case of drug in solution. But, in case of drug in nanoparticles as the concentration of paclitaxel was increased from 1 ng to 1000 ng/ml the cell viability percentage decreased from 85% to about 35% (FIG. 15a). Similarly, in case of rapamycin in drug solution the percentage of cell viability was decreased from 65% to 37% and the drug in nanoparticles showed a decrease from 63% to 40% (FIG. 15b). In case of combinational drug formulation, the free drug showed in decrease from 75% to 37% whereas the drug in nanoparticles showed a decrease in cell viability percentage from 70% to 27% (FIG. 15c). The paclitaxel loaded glyceryl monooleate (GMO) Magnetic nanoparticles (MNPs) and the paclitaxel in solution showed similar $IC_{50}$ values. But the rapamycin loaded glyceryl monooleate (GMO) Magnetic nanoparticles (MNPs) showed a significantly higher $IC_{50}$ value than that of the drug in solution (58.8 ng/ml vs. 84.2 ng/ml). But the combination drug formulation showed similar $IC_{50}$ values as that of the combination drugs in solution (Solution—21.99 ng/ml vs. MNP—16.6 ng/ml) (FIG. 16).

The MNPs have a proven candidacy for its biocompatibility and its wide application in the field of medical sciences.

Therefore, a novel monodispersed water soluble MNP formulation was developed in which hydrophobic anticancer drugs can be loaded efficiently. To prevent MNPs from aggregation and opsonization in a biological solution, it must have a polymeric Coating on its surface. Before loading of drugs the magnetic nanoparticles are generally surface modified with hydrophilic polymers such as starch or dextran, PEG, PLL, PEI, and the therapeutic agents of interest is either chemically conjugated or ionically bound to the outer layer of polymer so as to improve their biocompatibility and stability.

To obtain better aqueous dispersibility, several groups have used surfactants like pluronic, as the amphiphilic molecule which forms a coating on the surface of the iron oxide nanoparticles. Using the surfactant pluronic F-127, Jain et al have successfully developed an aqueous based formulation of iron oxide with hydrophobic drug loading. The aqueous dispersibility of the MNPs is achieved by the anchorage of the pluronic F-127 at the interface of OA shell surrounding the iron oxide particles. Experimental studies show that higher doses of pluronic F-127 has the toxic effect to human erythrocytes. When the pluronic was used as emulsifying agent for the drug amphotericin-B, there is detectable cell lysis of human erythrocytes at the concentration of 16 μg/ml. It has also been experimented that use of Pluronic F-127 at higher doses shows an elevation of cholesterol and triglycerides in the blood plasma.

Therefore we have developed a novel formulation using long chain polymer having a little affinity towards the aqueous base, so that the toxic effect of the surfactant can be avoided. Our formulation gives a well aqueous dispersibility without the use of any surfactant. During the synthesis process of the iron oxide nanoparticles the organic solvents play a vital role in removing the excess amount of GMO coating and keeping a balance between the hydrophobicity required for drug attachment and hydrophilicity required for making a water dispersible formulation. In our formulation, a mixture of ethyl acetate and acetone in 70:30 (v/v) ratio is helpful to maintain this balance. As both the solvents are aprotic they help to remove the excess hydrophobic coating from the magnetic nanoparticle surface.

In our MNP formulation the hydrophobic drug is partitioned in the form of distribution in the GMO crust surrounding the iron oxide nanoparticles (FIG. 13). This method has the advantage of offering greater flexibility of loading hydrophobic drug either alone or in combination. GMO, on the other hand, forms liquid crystal in the presence of water. In our formulation of glyceryl monooleate (GMO) Magnetic nanoparticles (MNPs), after washing by organic solvent mixture the free GMO gets removed by leaving behind layers of GMO which are adsorbed onto the surface of MNPs. Our result demonstrated that the GMO is well partitioned and chemisorbed as an attachment of carboxylate head groups on the surface of iron oxide nanoparticles. It is also reported that the magnetic nanoparticles prepared by co-precipitation method have enormous hydroxyl groups on the surface. Since the nanoparticles possess a high surface to volume ratio, therefore the surface hydroxyl groups readily reacts with the carboxylic groups of the GMO molecules at higher temperature. During the formulation process the GMO gets chemisorbed on the surface of the MNPs to make the first layer through electrostatic interaction between the carboxyl, head groups of GMO and hydroxyl groups of MNPs. Further layers of GMO on the surface of MNPs are very weak which are only due to adsorption and not by any electrostatic interaction. Similar chemisorption of drug was achieved with the cobalt nanoparticles in the presence of fatty acids.

The adsorption of the GMO has been confirmed by FT-IR analysis. In the pure GMO there is presence of C=O stretch at ~1730 $cm^{-1}$. In the GMO coated MNPs the vibrational stretch of COO— was observed at 1400 $cm^{-1}$ instead of C=O stretch. This shows the chemisorption of GMO on the surface of MNPs. Similar results were also observed by other groups working on OA coated MNPs. In their study, after adsorption of OA on the MNP surface no peaks relating to C=O was found. Instead, peaks for asymmetric and symmetric stretches of COO were found which are due to the chemisorption of the carboxylic group in carboxylate form. In our formulation, the OH groups of the GMO may have contributed for the better water dispersibility as the FTIR results show that the vibrational stretch for OH group at 3400 $cm^{-1}$ gradually increases with increase in percentage of GMO coating. This is attributed to the adsorption of GMO on the surface of the MNPs as explained in (FIG. 4, f).

Zeta potential is a bulk property that is not sensitive to the changes in the surface chemistry. The magnitude of the zeta potential gives an indication of the potential stability of the colloidal system. If all the particles in suspension have a large negative or positive zeta potential then they will tend to repel each other and there will be no tendency for the particles to aggregate. The zeta potential of glyceryl monooleate (GMO) Magnetic nanoparticles (MNPs) in our formulation shows a high positive value ~30 mV. The zeta potential of the MNPs did not change significantly with the increase of the GMO coating and also after loading of the drug to the glyceryl monooleate (GMO) Magnetic nanoparticles (MNPs).

The use of polymer coated nanoparticles have limited applications because of less drug loading capacity particularly with hydrophobic anti cancer drugs. A group has shown that the mitoxantrone drug was ionically attached to the starch coated magnetic nanoparticles modified with phosphate groups. But the dissociation of drug from the particles comes after ~60 minutes under in vitro condition. Also the amount of drug associated with the formulation is very low (0.8 wt %). In our formulation, the drug load is quite high around (7.5 wt %). Ideally for the effective treatment, the drug delivery vehicle should carry the heavy payload so that it can systemically and effectively dissociate the drugs to the affected tissues. We have formulated paclitaxel, rapamycin and combination of drugs in glyceryl monooleate (GMO) Magnetic nanoparticles (MNPs) formulations and achieved higher entrapment efficiency (more than 75%). The drug loaded glyceryl monooleate (GMO) Magnetic nanoparticles (MNPs) exhibit a sustained release and dose dependent cytotoxicity activity in the cancer cells. Earlier Rudge et al have also observed the dose dependant antiproliferative effects of the magnetically targeted carriers loaded with doxorubicin on SK-Br3 cell. The in vitro release study was carried out to estimate the amount of drug releasing from the glyceryl monooleate (GMO) Magnetic nanoparticles (MNPs). The anticancer drug loaded to the MNPs probably diffuses out from the polymeric shell under the influence of the concentration gradient, similar observation was observed in OA coated iron oxide nanoparticles.

Our formulation offers the aqueous dispersibility and the flexibility of most effective partitioning of hydrophobic drug either alone or in combination to the glyceryl monooleate (GMO) Magnetic nanoparticles (MNPs) with exclusion of the surfactants. We have prepared paclitaxel and rapamycin loaded glyceryl monooleate (GMO) Magnetic nanoparticles (MNPs), and a combination of both. The encapsulation efficiency was around 75%. From this it seems possible that large amount of drugs is feasible to be partitioned into the glyceryl monooleate (GMO) Magnetic nanoparticles (MNPs). Thus our formulation can also be used for combination drug therapy which shows synergistic effect of different drugs so that low dose drug can be used. A combination of drugs is significantly more effective than either drug alone having a dramatically longer effect on cancer. Our result demonstrated that the $IC_{50}$ value of rapamycin was quite higher in the nanoparticles formulation (84.2 ng/ml). In the combined drug formulation the $IC_{50}$ value has significantly decreased compared to individual drug (16.6 ng/ml). This decrease in $IC_{50}$ value in combined drug formulation gives an opportunity for using lower doses of drugs, which will minimize the toxicity towards the healthy cells. The combined drugs in solution also showed a lower $IC_{50}$ value (21.99 ng/ml). However the glyceryl monooleate (GMO) Magnetic nanoparticles (MNPs) formulation allocates delivering same ratios of both the drugs at the target site.

In our glyceryl monooleate (GMO) Magnetic nanoparticles (MNPs) formulations it can be observed that the $IC_{50}$ value of drugs in nanoparticles are more or less same as that of the drugs in solution. This probably suggests the sustained release of the drugs from the particulate system as only a small fraction of the adsorbed drug gets released during the experimental period of 5 days. This may help in preventing cancer from relapsing and drug resistance. Also this will prevent degradation of the drugs before accumulation of the particles at the target site.

Magnetic nanoparticles due to their magnetic property are Very useful in different biomedical applications like cell separation, drug targeting or targeting of specific biomolecules. For such processes, the surfaces of the MNPs have to be altered with specific targeting moieties. The targeting moieties or the biomolecules require specific functional groups like carboxylic group or amine groups to get attached on the MNP surfaces. In our formulation, we have functionalized the glyceryl monooleate (GMO) Magnetic nanoparticles (MNPs) with carboxylic groups by coating the glyceryl monooleate (GMO) Magnetic nanoparticles (MNPs) with DMSA. The functionalization of MNPs was confirmed by FTIR analysis. After coating to the MNPs, the carbonyl stretch at 1700 $cm^{-1}$ of DMSA gives a COOH stretch at around 1650 $cm^{-1}$. As the concentration of DMSA increases, vibrational modes at around 1376 $cm^{-1}$ and 1650 $cm^{-1}$ assigned to C—O stretch and COOH stretch respectively gets increased. Also another peak at around 1715 $cm^{-1}$ can be observed at higher concentration of DMSA. This refers to the C=O stretch which reveals the existence of DMSA. These results also coincide with the work of other groups working on DMSA to get carboxyl group functionalized nanoparticles. These functionalized glyceryl monooleate (GMO) Magnetic nanoparticles (MNPs) can be used for different applications like lysozyme immobilization, uptake by smooth muscle cells.

Therefore, the colloidal carrier system is one of the preference mode of targeting the tumors by anticancer drugs through enhanced permeation retention (EPR) effect. As the tumors have leaky vasculature and impaired lymphatic drainage, the intravenously injected colloidal Carrier extravasate and accumulate in the tumor tissues. For successful targeting to the tumors the magnetic nanoparticles must escape the uptake by the RES and circulate in the blood for prolong period of time. Hydrophilic polymers like Pluronic, polyethylene glycol are used to change the surface property of the colloidal nanoparticles so that they can evade the uptake by the RES by making them "stealth". The delivery of hydrophobic anticancer drugs through the systemic circulation is a challenge. Various drug delivery vehicles such as micelles, emulsions and nanoparticle formulations have been investigated to address these problems. However the iron oxide nanoparticles are well tolerated by body and degrade with time.

TABLE 1

Effect of different solvents on synthesis of Iron oxide particles

| Sl. No. | Washing solvent | Size in water | Size in n-Hexane |
|---|---|---|---|
| 1 | Acetone (100%) | 188.5 ± 11 | 177 ± 21 |
| 2 | Ethyl acetate (100%) | 280.3 ± 23 | 130.9 ± 10 |
| 3 | Diethyl ether (100%) | 268.8 ± 17 | 122.8 ± 15 |
| 4 | Chloroform (100%) | 112.9 ± 19 | 52.83 ± 21 |
| 5 | Ethyl acetate:Acetone (50:50) | 197.8 ± 32 | 166.9 ± 17 |
| 6 | Ethyl acetate:Acetone (70:30) | 143.5 ± 17 | 120.3 ± 11 |

TABLE 2

Effect of GMO on Magnetic properties of Iron oxide nanoparticles.

| Samples | Saturation magnetization Ms (emu/g) at 10K | Saturation magnetization Ms (emu/g) at 300K | Coercive filed Hc (Oe) |
|---|---|---|---|
| Native Iron oxide (MNP) | 57 | 66 | 349.89 |
| MNP + 100 μl GMO | 69.8 | 54 | 350.04 |
| MNP + 560 μl GMO | 67 | 52.5 | 349.98 |

TABLE 3

The d-spacing values (nm) calculated from the electron diffraction pattern in FIG. 9 and the standard atomic spacing for $Fe_2O_3$ along with respective hkl indexes from the JCPDS card (19-0629).

| Ring | Calculated d Spacing | JCPDS data for $Fe_3O_4$ | hkl |
|---|---|---|---|
| 1 | .4857 | .4852 | 111 |
| 2 | .3003 | .2967 | 220 |
| 3 | .2558 | .2532 | 311 |
| 4 | .2064 | .2099 | 400 |
| 5 | .1731 | .1714 | 422 |
| 6 | .1627 | .1615 | 511 |
| 7 | .1499 | .1484 | 440 |

TABLE 4

Physical characterization of different drug formulations in water

| Sample | Size (nm) | Polydispersity Index | Zeta potential (mV) |
|---|---|---|---|
| GMO-MNP (100%) | 152 ± 4.5 | 0.3 ± 0.07 | 36 ± 3.1 |
| Paclitaxel-GMO-MNP | 246.9 ± 3.7 | 0.23 ± 0.01 | 22.6 ± 6.9 |
| Rapamycin-GMO-MNP | 200.9 ± 5.2 | 0.37 ± 0.003 | 24.8 ± 4.2 |
| Combo-GMO-MNP | 187.2 ± 4.2 | 0.41 ± 0.06 | 26.3 ± 5.7 |

EXAMPLES

Example 1

Materials

Iron (III) chloride hexahydrate ($FeCl_3.6H_2O$) pure granulated, 99%, Iron (II) chloride tetrahydrate ($FeCl_2.4H_2O$) 99%, Ammonium hydroxide, 2,3 meso mercapto Succinic Acid (DMSA), Tween 80, Pluronic F-127, span series, stannus chloride, mercuric chloride, orthophosphoric acid, potassium dichromate and potassium bromide were purchased from Sigma-Aldrich (St. Louis, Mo.). Glyceryl monooleate was procured from Eastman (Memphis, Tenn.). FITC-BSA (Albumin from Bovine Serum Flurescien conjugated) was procured from Invitrogen Corporation, Carlsbad, Calif., USA. N-(3-Dimethylaminopropyl)-N'-ethyl-Carbomdiimide hydrochloride (EDC) and N-HydroxySuccinimide (NHS) were procured from Fluka, Sigma Aldrich, Belgium. Barium diphenylamine sulphonate (BDAS) was procured from Acros Organics, Belgium. Paclitaxel, rapamycin were obtained from Shaanxi Schiphar Biotech Pvt Ltd, China. Magnet NdFeB (12200 G) procured from Edmund Scientific, Tonawada, N.Y.). All other chemical used were of reagent grade obtained from Sigma. MilliQ water purged with nitrogen ($N_2$) gas was used in all steps involved in the synthesis and formulations of magnetic nanoparticles.

Example 2

Synthesis of Magnetic Nanoparticles

Synthesis of magnetic particles were done according to the protocol of Jain et al with little modifications. Accordingly, 0.1M Fe (III) (1.35 g $FeCl_3$ dissolved in 50 ml $N_2$ purged water) and 0.1M Fe (II) (0.99 g $FeCl_2$ dissolved in 50 ml $N_2$ purged water) were prepared. 15 ml of 0.1M Fe (III) and 7.5 ml 0.1M Fe (II) were mixed and heated at 80° C. for 10 minutes under constant stirring with a magnetic stirrer in $N_2$ atmosphere. 1.5 ml of ammonium hydroxide (14.5 M) was added to it. Then it was stirred for 20 minutes. Finally the precipitate was washed with $N_2$ purged water with Centrifugation at 20,000 rpm for 20 minutes at 10° C. (Sigma centrifuge, 3-16PK, Germany). The pellets were dispersed in 5 ml of MilliQ water and frozen at −80° C. and were lyophilized using a lyophilizer (LABCONCO Corporation, USA) for two days at temperature of −48° C. and 0:05 mbar. The MNP yield was determined by weighing the lyophilized powder and was found to be 110 mg.

Example 3

Formulations of Magnetic Nanoparticles

Different formulations of iron oxide nanoparticles were developed by the following protocol. 15 ml 0.1 M Fe (III) and 7.5 ml 0.1 M Fe (II) was mixed and heated at 80° C. with constant stirring. 1.5 ml of ammonium hydroxide (14.5 M) was added drop wise to it. Then GMO was added to the suspension drop wise. To study the amount of concentration of GMO required to coat the MNPs, we have prepared different formulations (different weight percentage of GMO to MNP yield were added i.e, 12-560 µl of GMO was added to get 10-504% of GMO coated MNPs). The mixture was allowed to stir for 20 minutes at 80° C. under a $N_2$ atmosphere to evaporate the excess amount of ammonia from the formulation. It was washed with different solvents and centrifugation for 20 minutes at 10° C. at 20,000 rpm (Sigma centrifuge, 3-16PK, Germany). Washing was repeated for 3 times. The washings of the excess GMO from the magnetic nanoparticles is critical to get a better aqueous dispersibility. 'To study the effect of different solvent washings on the GMO coated' magnetic nanoparticles (GMO-MNPs), different solvents like acetone, ethyl acetate, diethyl ether, chloroform, and mixture of different solvents in different ratio like ethyl acetate:acetone (50:50 and 70:30) were used during the washing steps. The pellets were lyophilized for two days at temperature of −48° C. and 0.05 mbar to get the powder form.

The study the effect of different surfactants on aqueous dispersity of GMO-MNPs, 10 mg of GMO-MNPs were taken and dissolved in 10 ml of MilliQ water and was sonicated for 1 minutes at 55 watt (VC505, Sonics Vibracell, Sonics and Materials Inc., USA). To this different surfactants were added in the ratio of particle:surfactant (1:1) and was allowed for over night stirring in a closed container to minimize exposure to atmospheric oxygen to prevent oxidation of the MNPs. These particles were washed 3 times with water to remove the surfactants which were not bounded to the MNPs by magnetic decantation and lyophilized to get the powder form for further use.

Example 4

Characterization of GMO-MNPs

Particle Size Determination by Dynamic Light Scattering and ζ Potential Measurements.

Dynamic light scattering (DLS) was used to measure the hydrodynamic diameter and Laser Doppler Anemometry (LDA) was used to determine the zeta potential (mV) of GMO-MNPs. The DLS and LDA analysis were performed using a Zetasizer Nano ZS (Malvern Instruments, Malvern, UK). The particle size measurement was done by dispersing MNPs (~1 mg/ml) in MilliQ water using water bath sonicator for 1 minute and then the suspension was diluted (100 µl to 1 ml) and the size was measured in polystyrene cuvette using the Zetasizer Nano ZS. To compare the size of the MNPs in organic solvent, the measurement of particle size in n-hexane was made following the same procedure using the quartz cuvette. To further see the effect of size in respect to the different surfactants added to the GMO-MNPs (~1 mg/ml) surfactant coated GMO-MNPs were suspended in MilliQ water and sonicated using water bath sonicater for 1 minute at 55 watt (VC505, Sonics Vibracell, Sonics and Materials Inc., USA) and further diluted (100 µl to 1 ml) for particle size measurement. The same suspension in MilliQ water was used for measuring the zeta potential of MNPs.

Transmission Electron Microscopy (TEM).

The internal structure of MNPs were determined by TEM measurements for which a drop of diluted solution of the GMO-MNPs (either in water or n-Hexane) was placed in carbon-coated copper TEM grid (150 mesh, Ted Pella Inc, rodding, CA) and was allowed to air-dry. The samples were imaged used a Philips 201 transmission electron microscope (Philips/FEI Inc., Barcliff, Manor, N.Y.). The TEM photograph was taken by using the NIH imaged software. To calculate the mean particle diameter, 50 particles were taken for measurement.

X-ray Diffraction (XRD)

XRD analysis was carried out to know the crystallinity of the MNPs formed. The lyophilized samples (~500 mg) of native iron oxide particles and 100% GMO-MNPs were carried out using a Brucker D4 Endeavour, with Bragg-Brentano-Brentano parafocusing geometry. The analysis was done with copper target X-ray tube with Cu Kα radiations. The parameters chosen for the measurement were 20 steps of 0.08°, 1 second of counting timer per step, and 2θ range from 10.01° to 69.53°.

Determination of Iron content in the magnetic nanoparticle formulations. To determine the percentage of iron present in the MNP formulations, the chemical analysis of the samples was carried out by recommended analytical procedure. Different GMO-MNP formulations (in triplicate) were subjected to di-acid digestion for wet chemical analysis. The MNP formulations (~50 mg) were first digested by adding 2 ml concentrated HCl followed by heating at 60° C. for 10 minutes. Then the digested product was diluted to 25 ml with MilliQ water. To the above diluted sample (5 ml), 2 ml of concentrated HCl was added and heated at 60° C. for 10 minutes. 4 ml of 0.25 M stannus chloride was added drop wise to the digested product up to decolouration. Then the sample was cooled to room temperature and 2 ml of saturated mercuric chloride was added and was mixed well by shaking. To the mixture, 10 ml of Zimmerman-Reinhard reagent (5 ml of 5% sulphuric acid and 5 ml of orthophosphoric acid) was added followed by addition of 10 ml of MilliQ water. Finally, the iron content in the formulation was analyzed volumetrically by titrating against 0.01 N potassium dichromate solution using barium diphenylamine sulfonate (BDAS) indicator.

Fourier Transform Infrared Spectroscopy (FT-IR).

FT-IR measurement was carried out to know the chemical interactions in the MNP formulations. FT-IR (Perkin Elmer, FTIR Spectrometer, SPECTRUM RX I) was used to characterize the surface composition of the different formulations of MNPs. Each spectrum was obtained by averaging 32 interferograms with resolution of 2 cm$^{-1}$ in the range of 400 to 4000 cm$^{-1}$. A small amount of MNPs (either native or formulated) were milled with KBr, and a mixture of them was pressed into a pellet for analysis with a pressure of 150 kg/cm$^2$.

Magnetization Studies

In order to quantify the amount of magnetism present in the formulated MNPs magnetization study was carried. The Magnetic properties were investigated by a Superconducting Quantum Interference Device (SQUID) magnetometer (MPMS5, Quantum Design) with fields up to 1.5 T and temperatures of 10 K and 300 K respectively. Zero-field-cooled (ZFC) and field-cooled (FC) magnetization measurements were carried out as a function of temperature. To determine the ZFC measurements the samples were cooled from 300 K to 10 K in zero field as a function of temperature at 100 Oe field strength as gradually warmed. To take the FC measurement, the sample as cooled in the measuring field. The magnetization was determined as a function of field M (H) at 10 and 300 K. By putting the magnetization curve in an analytical ferromagnetic model and by normalizing the diamagnetic contribution (x) due to the background the saturation magnetization (Ms) and the Coercive field (Hc) were determined.

Example 5

Drug Loading in the Formulation

Loading of Anticancer Drugs in Magnetic Nanoparticles.

To exploit the MNP formulations as a drug delivery vehicle, anticancer drugs were taken into account. For the incorporation of anticancer drugs in GMO-MNPs, paclitaxel, rapamycin and a combination of both (paclitaxel and rapamycin) were used. We have used 100% GMO coated MNPs for drug loading. 100 mg of the GMO-MNPs were dispersed in 10 ml. MilliQ water and was sonicated for 1 minute. The drugs were dissolved in organic solvent acetonitrile either individually or in combination (10% w/w to the polymer i.e, 10 mg of either of the drugs dissolved in 1 ml or 1 ml of combined drugs, 5 mg each). The drug was added drop wise to the GMO-MNPs suspension and kept for overnight stirring with a magnetic stirrer to allow the partitioning of the drug into the GMO shells surrounding the magnetic nanoparticles. The unpartitioned drugs were washed with water and were separated by centrifuging the particle suspension at 13,800 rpm for 10 minutes at 10° C. (Sigma centrifuge, 3-16PK, Germany). Washing was repeated for 3 times for the complete removal of the unentrapped drug. The pellets were lyophilized for quantification of entrapment efficiency of different drugs through reverse phase high performance liquid chromatography (RP-HPLC).

Quantification of Drug by RP-HPLC.

Quantification of the drug incorporated in the MNPs, was carried out through RP-HPLC. The estimation of the amount of drug entrapped in the GMO-MNPs was done by direct method. To the lyophilized nanoparticles solvent acetonitrile (1 mg/ml) was added and sonicated in an ice bath for 1 minute, at 55 watt and kept in shaker for 24 hours for the drug to come out from the particles. Then the nanoparticles were centrifuged for 10 minutes at 13, 800 rpm at 10° C. (Sigma microcentrifuge, 1-15PK, Germany). Supernatants were taken out for the estimation of drug entrapped. The analysis of sample was done by reverse phase isocratic mode of HPLC with little modification using Agilent 1100 (Agilent technologies, Waldbronn Analytidal Division, Germany) which consists of a column (Zorbax Eclipse XDB-C18, 150×4.6 mm, i.d). 20 µl of different drug samples were injected manually in the injection port and were analyzed with the mobile phase of acetonitrile:water (80:20 v/v), which was delivered at flow rate of 1 ml/min with a quaternary pump (Model No—G1311A) at 25° C. with thermostart (Model No—G1316A). The drug levels were quantified by UV detection at 228 nm for paclitaxel and 278 nm for rapamycin with a detector (DAD, Model —G 1315A). The amount of drug (paclitaxel and rapamycin) in samples was determined from the peak area correlated with the standard curve. The standard curves of paclitaxel and of rapamycin were prepared under identical conditions. The entrapment efficiency was calculated from the following formula reported earlier % of Entrapment Efficiency=(drug loaded in nanoparticles/drug added in formulation)×100

Example 6

Kinetics of Paclitaxel and Rapamycin Release from Magnetic Nanoparticles

To know the amount of drug released in in vitro condition a kinetics measurement was done. The release of drugs from GMO-MNPs was carried out by dissolving 10 mg of nanoparticles in 3 ml of PBS (ph=7.4, 0.01 M, containing 0.1% w/v of Tween 80). Tween 80 was used in the buffer to maintain the sink condition during the release study. It was mixed properly by vortexing and then was divided into 3 parts, 1 ml each. All the samples were kept in an orbit shaking incubator (Wadegati Labequip, India) at 37° C., rotating at 150 rpm. The samples were removed at predetermined time intervals and centrifuged at 13,800 rpm for 15 minutes at 10° C. (Sigma microcentrifuge, 1-15PK, Germany) to get the supernatant. Then the pellets were dispersed with the same volume of fresh PBS (pH=7.4, 0.01 M PBS, containing 0.1% w/v of Tween 80) and vortexed and kept in shaker. The collected supernatants were lyophilized for 48 hours, and then were dissolved in acetonitrile and centrifuged at 13, 800 rpm for 10 minutes at 4° C. (Sigma microcentrifuge, 1-15PK, Germany). The obtained supernatant was taken out and injected in the RP- HPLC to determine the amount of drug released either paclitaxel, rapamycin or combination of both with respect to different time intervals.

Example 7

Cell Culture

The cell culture experiments were carried out in MCF-7 (breast cancer) cell line purchased from American Type Culture Collection (ATCC, Manassas, Va.) were grown in RPMI 1640 medium (Himedia Laboratories PVT. LTD., Mumbai, India) supplemented with 10% fetal bovine serum (Himedia Laboratories Pvt. Ltd., Mumbai, India) and 100 µg/ml penicillin G and 100 µg/ml streptomycin (Gibco BRL, Grand island, NY) at 37° C. in a humidified and 5% $CO_2$— atmosphere (Hera Cell, Thermo Scientific, Waltham, Mass.).

Example 8

Statistical analyses were performed using a Student's t test. The differences were considered significant for p values of <0.05.

Example 9

Mitogenic Assay.

To find out the cytotoxicity of the anticancer drugs, mitogenic assay was carried out. The MCF-7 cells were seeded at 5,000 per well in 96 well plate (Corning, N.Y., USA) and kept in the incubator for 24 hours for better cell attachment. Different concentrations of paclitaxel, rapamycin or combination of the drug (0.1 µM to 1000 µM), either in solution or loaded in GMO-MNPs were added. GMO-MNPs without drug and medium were used as respective controls. The medium was changed on 2nd and 4th days following the drug treatment; no further dose of drug was added. Viability of the cells was determined at 5th day. After the specified incubation time, 10 µl MTT (Sigma) was added, and the plates were incubated for 3 hours at 37° C. in a cell culture incubator (Hera Cell, Thermo Scientific, Waltham, Mass.), following which the intracellular formazan crystals were solubilized in dimethyl sulfoxide and the color intensity was measured at 540 nm using a microplate reader (Synergy HT, BioTek Instruments, Inc., Winooski, Vt.). The antiproliferative effect of different treatments was calculated as a percentage of cell growth with respect to respective controls.

Example 10

Surface Functionalization of Magnetic Nanoparticles

MNPs are difficult to bond with biomolecules in aqueous solution. Therefore, to attach any biomolecule on to the surface of the MNPs, the surface should be functionalized with different functional groups like carboxylic or amine group. To attach any peptide or protein on to the surface of the MNPs, the particles should be surface functionalized with carboxylic groups. Therefore, 2, 3 meso mercapto succinic acid (DMSA) was used to functionalize the GMO-MNPs with carboxylic acid group. 500 mg of MNP-GMO was added to 5 ml of 0.2 M DMSA dissolved in DMF and kept for 24 hours stirring in a magnetic stirrer. The sample was washed with ethanol 3 times by centrifuging at 13,800 rpm at 10° C. for 20 minutes and the pellets were lyophilized. To find out the effect of DMSA in the functionalization of GMO-MNPs, we have used different concentrations of DMSA solutions (0.4-3.2 M) and followed the above procedure to get the lyophilized powder.

Acid Number Determination.

For, the quantification of free carboxylic acid groups attached on the surface of MNPs, acid numbers of the GMO-MNPs were determined following the experimental protocol by Garkhal et al. 20 mg of the different concentration of DMSA coated GMO-MNPs were initially treated with 5 ml NaOH (1 N) for 30 minutes to cleave some of the surface ester bonds to generate free carboxylic ends. Then the samples were washed 3 times with MilliQ water by centrifuging at 13,800 rpm at 10° C. for 20 minutes. Then all the samples were vacuum dried by lyophilizer. Free acid groups present on the GMO-MNPs surface were quantified by taking nanoparticle solution 1 mg/ml and diluting to 50 times. Then the diluted solution was titrated against NaOH (0.0005 N). NaOH solution is to be standardized before by titrating against oxalic acid. Acid number was calculated by the following formula.

$$A = \frac{\text{Volume required during titration} * \text{Normality of NaOH} * 40 \text{ (Mol. Wt. Of NaOH)}}{\text{Weight of nanoparticles (g)}}$$

Example 11

Conjugation of FITC-BSA

FITC BSA was conjugated to the carboxyl groups, which were functionalized on the surface of GMO-MNPs. For conjugation, 10 mg of functionalized GMO-MNPs were added to 5 ml of PBS (pH=7.4, 0.02 M). 250 µl of EDC and 250 µl of NHS in PBS (pH=7.4, 0.02 M, 1 mg/ml) was added to it. The sample was left in room temperature under magnetic stirring for 4 hours. Then the sample was magnetically decanted to remove free EDC and NHS. To the pellet 3 ml of PBS (pH=7.4, 0.02 M) and 100 µl of FITC-BSA (1 mg/ml) was added. The solution was left for 2 hours and then incubated at 4° C. overnight. Next day magnetic decantation was done and the pellets were washed 2 times with PBS (pH=7.4, 0.02 M) to remove any unconjugated FITC-BSA. A standard plot for FITC-BSA was prepared taking concentrations 2.5-20 µg/ml at $\lambda_{ex}$=488 nm and $\lambda_{em}$=520 nm using a fluorescence microplate reader (Synergy HT, BioTek Instruments, Inc., Winooski, Vt.). The percentage of conjugation of FITC-BSA to the GMO-MNPs was calculated by indirect method. First, the amount of un-conjugated FITC-BSA present in the supernatant was determined by taking the fluorescence measurement and using the standard plot of FITC-BSA. Then the amount of un-conjugated FITC-BSA was deducted from the total FITC-BSA amount added to get the amount of conjugated FITC-BSA.

The invention claimed is:
1. A method for preparing glyceryl monooleate (GMO) magnetic nanoparticles (MNPs) formulation comprising:
heating a mixture of Fe (III) and Fe (II) with constant stirring under $N_2$ atmosphere;
adding ammonium hydroxide to the said mixture;

adding glyceryl monooleate (GMO) to the suspension drop wise;

subjecting the mixture to the step of stirring under $N_2$ atmosphere;

washing the formulation several times with a solvent mixture comprising ethyl acetate: acetone (70:30 v/v) to wash excess glyceryl monooleate (GMO); and subjecting the washed formulation to lyophilization to yield powder form.

2. The method as claimed in claim 1, wherein the mixture of Fe (III) and Fe (II) is heated at 80° C.

3. The method as claimed in claim 1, wherein 12-560 µl of GMO is added to get 10-504% of GMO coated MNPs.

4. The method as claimed in claim 1, wherein the step of subjecting the mixture to the step of stirring under $N_2$ atmosphere comprises stirring the mixture for 20 minutes at 80° C. under $N_2$ atmosphere to evaporate excess ammonia from the formulation after adding the GMO drop wise.

5. The method as claimed in claim 1, wherein the solvent mixture consists of ethyl acetate: acetone (70:30 v/v).

6. The method as claimed in claim 1, further comprising the step of dispersing the magnetic nanoparticles in water and sonicating for 1 minute.

7. The method as claimed in claim 1, wherein the step of washing with the solvent mixture comprising ethyl acetate: acetone (70:30 v/v) further comprises centrifugation for 20 minutes at 10° C. at 20,000 rpm.

8. The method as claimed in claim 1, wherein the step of washing is repeated for 3 times.

\* \* \* \* \*